United States Patent
Kumar et al.

(10) Patent No.: US 12,285,298 B2
(45) Date of Patent: Apr. 29, 2025

(54) INSTRUMENT TRACKING MACHINE

(71) Applicant: Stryker Corporation, Portage, MI (US)

(72) Inventors: Mayank Kumar, San Jose, CA (US); Sheetal Deepak Jantikar, Freemont, CA (US); Siddarth Satish, Portola Valley, CA (US); Kevin J. Miller, Mountain View, CA (US); Steven Scherf, Oakland, CA (US); Charles Peterson Carroll, Berkeley, CA (US)

(73) Assignee: Stryker Corporation, Portage, MI (US)

( * ) Notice: Subject to any disclaimer, the term of this patent is extended or adjusted under 35 U.S.C. 154(b) by 1128 days.

(21) Appl. No.: 17/158,353

(22) Filed: Jan. 26, 2021

(65) Prior Publication Data
US 2021/0236227 A1 Aug. 5, 2021

Related U.S. Application Data

(60) Provisional application No. 62/968,538, filed on Jan. 31, 2020.

(51) Int. Cl.
*A61B 90/00* (2016.01)
*A61B 90/90* (2016.01)

(52) U.S. Cl.
CPC ............ *A61B 90/08* (2016.02); *A61B 90/361* (2016.02); *A61B 90/90* (2016.02); *A61B 2090/0803* (2016.02)

(58) Field of Classification Search
CPC ....... A61B 90/08; A61B 90/361; A61B 90/90; A61B 2090/0803
(Continued)

(56) References Cited

U.S. PATENT DOCUMENTS 9,418,314 B2 8/2016 Nomura et al.
10,452,954 B2 10/2019 Schroff et al.
(Continued)

FOREIGN PATENT DOCUMENTS

CN 110051443 A 7/2019
CN 110506274 A 11/2019
(Continued)

OTHER PUBLICATIONS

"International Application Serial No. PCT/US2021/015070, International Search Report mailed Apr. 22, 2021", 2 pgs.
(Continued)

*Primary Examiner* — Aaron F Roane
(74) *Attorney, Agent, or Firm* — Howard & Howard Attorneys PLLC

(57) ABSTRACT

A machine accesses a first image captured prior to initiation of a procedure, where the first image depicts a set of instruments, as well as a second image captured after initiation of the procedure, where the second image depicts a proper subset of the set of instruments depicted in the first image. From the first and second images, the machine may determine that an instrument among the set of instruments depicted in the first image is not depicted among the proper subset of the set of instruments in the second image, and then cause presentation of a notification that indicates the instrument not depicted in the second image is missing. Alternatively, or additionally, the machine may determine whether
(Continued)

an instrument among the set of instruments was used in the procedure, and then cause presentation of a notification that indicates whether the instrument was used in the procedure.

20 Claims, 11 Drawing Sheets

(58) Field of Classification Search
USPC .......................................................... 606/1
See application file for complete search history.

(56) References Cited

U.S. PATENT DOCUMENTS

| | | | |
|---|---|---|---|
| 11,256,963 | B2 | 2/2022 | Katayama et al. |
| 2004/0031626 | A1 | 2/2004 | Morris et al. |
| 2007/0125392 | A1 | 6/2007 | Olson et al. |
| 2013/0113929 | A1 | 5/2013 | DeLand |
| 2013/0336554 | A1 | 12/2013 | Lewis et al. |
| 2016/0180195 | A1 | 6/2016 | Martinson et al. |
| 2016/0379504 | A1 | 12/2016 | Bailey et al. |
| 2018/0204323 | A1* | 7/2018 | Sayani ................. G06Q 10/087 |
| 2018/0338801 | A1 | 11/2018 | Barnett et al. |
| 2019/0311802 | A1 | 10/2019 | Kokubo et al. |
| 2019/0388182 | A1 | 12/2019 | Kumar et al. |

FOREIGN PATENT DOCUMENTS

| | | | |
|---|---|---|---|
| JP | 2019180822 A | 10/2019 | |
| WO | 2013115093 A1 | 8/2013 | |
| WO | 2017011646 A1 | 1/2017 | |
| WO | WO-2017173465 A1 * | 10/2017 | ............. A61B 46/10 |
| WO | 2018221599 A1 | 12/2018 | |

OTHER PUBLICATIONS

"International Application Serial No. PCT/US2021/015070, Written Opinion mailed Apr. 22, 2021", 12 pgs.

Uecker, et al., "Automated instrument tracking in robotically assisted laparoscopic surgery", Journal of image guided surgery 1.6, <https://www.tandfonline.com/doi/pdf/10.3109/10929089509106338>, (1995), 308-325.

English language abstract for CN 110506274 A extracted from espacenet.com database on Jun. 4, 2024, 2 pages.

English language abstract and machine-assisted English translation for CN 110051443 A extracted from espacenet.com database on Sep. 27, 2024, 17 pages.

English language abstract for JP 2019-180822 A extracted from espacenet.com database on Sep. 27, 2024, 2 pages.

English language abstract for WO 2013/115093 A1 extracted from espacenet.com database on Sep. 27, 2024, 2 pages.

English language abstract for WO 2018/221599 A1 extracted from espacenet.com database on Sep. 27, 2024, 2 pages.

Mitash, Chaitanya, et al., "A Self-supervised Learning System for Object Detection using Physics Simulation and Multi-view Pose Estimation", IEEE/RSJ International Conference on Intelligent Robots and Systems (IROS), (2017), 545-551.

Tremblay, Jonathan, et al., "Training deep networks with synthetic data: Bridging the reality gap by domain randomization", IEEE/CVF Conference on Computer Vision and Pattern Recognition Workshops, (2018), 1082-1090.

Zhou, Tian, "Surgical-Instrument-Dataset", 2021 GitHub, Inc., [Online]. Retrieved from the Internet: <URL: https://github.com/tian-zhou/Surgical-Instrument-Dataset/tree/master/instrument_recognition dataset>, (Jul. 6, 2017), 1 pg.

* cited by examiner

INSTRUMENT TRACKING MACHINE

RELATED APPLICATION DATA

This application claims the benefit of U.S. Provisional Patent Application No. 62/968,538 filed on Jan. 31, 2020, the contents of which are hereby incorporated by reference in their entirety.

TECHNICAL FIELD

The subject matter disclosed herein generally relates to the technical field of special-purpose machines that facilitate monitoring of instruments (e.g., surgical instruments or other tools), including software-configured computerized variants of such special-purpose machines and improvements to such variants, and to the technologies by which such special-purpose machines become improved compared to other special-purpose machines that facilitate monitoring of instruments.

BACKGROUND

A set of instruments (e.g., a set of surgical tools) may be arranged on a conveyance (e.g., a tray or a cart) and brought to a performer (e.g., a surgeon) of a procedure (e.g., a medical procedure, such as a surgical procedure) to be performed (e.g., on a patient). Not all instruments may be used during the procedure (e.g., 30%-80% of surgical instruments go unused), and it may be helpful to track which instruments were used and therefore warrant the time, effort, and costs of sterilization, and which instruments were not used. Regardless of use or non-use during the procedure, it may be beneficial to have all instruments present and accounted for after the procedure. For example, tracking surgical instruments during medical procedures can limit or reduce the risks of such instruments being inadvertently retained inside patients.

BRIEF DESCRIPTION OF THE DRAWINGS

Some embodiments are illustrated by way of example and not limitation in the figures of the accompanying drawings.

DETAILED DESCRIPTION

Figure 1:
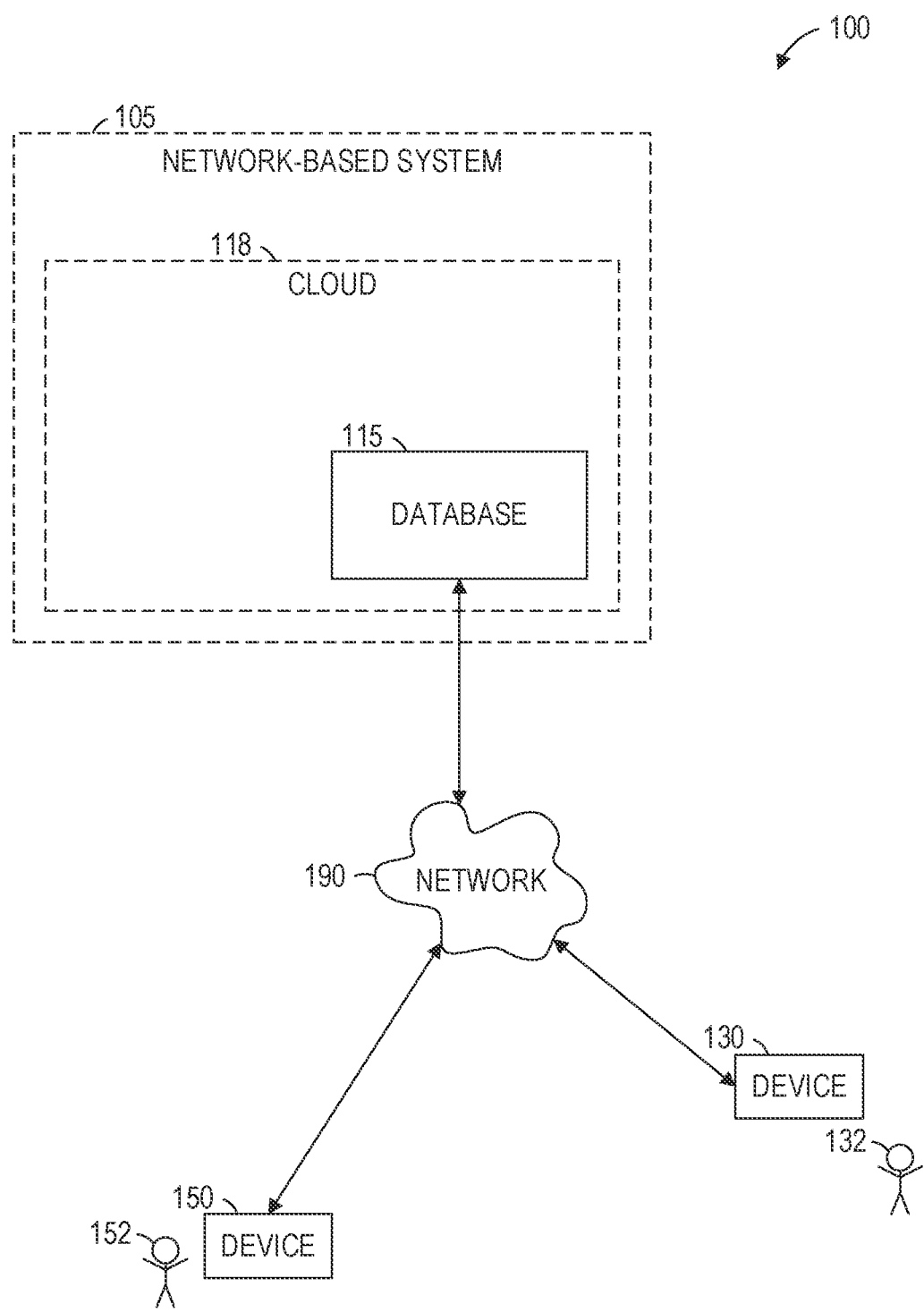
FIG. 1 is a network diagram illustrating a network environment suitable for operating an instrument tracking machine, according to some example embodiments.

Example methods (e.g., algorithms) facilitate detection, classification, identification, and tracking of instruments or other monitoring of instruments, and example systems (e.g., special-purpose machines configured by special-purpose software) are configured to facilitate detection, classification, identification, and tracking of instruments or other monitoring of instruments. Examples merely typify possible variations. Unless explicitly stated otherwise, structures (e.g., structural components, such as modules) are optional and may be combined or subdivided, and operations (e.g., in a procedure, algorithm, or other function) may vary in sequence or be combined or subdivided. In the following description, for purposes of explanation, numerous specific details are set forth to provide a thorough understanding of various example embodiments. It will be evident to one skilled in the art, however, that the present subject matter may be practiced without these specific details.

Precise and accurate detection, classification, and identification of instruments may be worthy goals in providing cost-effective management of instrument inventory, providing health and safety (e.g., for patients undergoing medical procedures), or both. Instrument usage information can help hospital management update, for example, instrument trays to only contain surgical instruments likely to be used (e.g., for a specific procedure, by a specific surgeon, or both). For such purposes, a machine (e.g., a device configured with suitable software, such as a suitable app) is configured to function as an instrument tracking machine and perform instrument detection, instrument classification, instrument identification, instrument tracking, or any suitable combination thereof, for one or more instruments based on images captured before and after initiation of a procedure (e.g., a medical procedure). As used herein, "instrument detection" refers to detecting that an instrument with unspecified type and unspecified identity is depicted at a location within an image; "instrument classification" refers to identifying, recognizing, or otherwise obtaining the type of a detected instrument; and "instrument identification" refers to identifying, recognizing, or otherwise obtaining the identity of a specific individual instrument in particular, in contrast with the identities of other individual instruments of the same type.

Configured in accordance with one or more of the example systems and methods discussed herein, the machine may function as an instrument classifier configured to determine a type (e.g., a classification or a category) for each instrument (e.g., scissors or forceps) depicted in an image (e.g., for counting instances of each type of instrument), an object identifier configured to identify a specific individual object (e.g., along with detection, classification, or both), such as a particular instrument (e.g., the same scissors previously depicted in a previous image or the same forceps previously depicted in a previous image), or both. For surgical instruments, examples of instrument types include graspers (e.g., forceps), clamps (e.g., occluders), needle drivers (e.g., needle holders), retractors, distractors, cutters, specula, suction tips, sealing devices, scopes, probes, and calipers.

Whether implemented as a portable (e.g., mobile) handheld device (e.g., a smartphone configured by an app), a portable cart-mounted or backpack-mounted device, a stationary machine (e.g., built into a hospital operating room, such as into a wall or a ceiling), or any suitable combination thereof, the machine accordingly may distinguish between or among different types of instruments, different individual instances of instruments, or both. In example situations involving a large collection of surgical instruments, the machine (e.g., functioning as an instrument classifier) may act as an identification tool to quickly find the corresponding types of several instruments by scanning them in real time.

In example situations where inventory management is important, the machine may provide an instrument tracking function. For instance, the operating rooms in many hospitals are often faced with the challenge of preventing retention of any surgical instruments within patients after their surgical procedures, which unfortunately is a common problem for hospitals. To address this challenge and avoid such accidents, the machine (e.g., functioning as an object identifier) may be deployed to identify and count surgical instruments, individually or by type, before and after initiation of a procedure (e.g., before initiation of the procedure and after completion of the procedure), to determine whether all instruments present at the beginning of the procedure are accounted for before closing up the patient.

According to some example embodiments of the systems and methods discussed herein, a suitably configured machine accesses a first image captured prior to initiation of a procedure, where the first image depicts a set of instruments available for use in the procedure. The machine further accesses a second image captured after initiation of the procedure (e.g., midway during the procedure, just before completion of the procedure, or after completion of the procedure), where the second image depicts a proper subset of the set of instruments depicted in the first image. From these images, the machine determines that an instrument among the set of instruments depicted in the first image is not depicted among the proper subset of the set of instruments in the second image. The machine then causes presentation of a notification that indicates the instrument depicted in the first image but not depicted in the second image is missing from the set of instruments.

According to certain example embodiments of the systems and methods discussed herein, a suitably configured machine accesses a first image captured prior to initiation of a procedure, and the first image depicts a set of instruments available for use in the procedure. The machine further accesses a second image captured after initiation of the procedure (e.g., partway through the procedure, shortly before completion of the procedure, or after completion of the procedure), and the second image depicts a subset of the set of instruments depicted in the first image. From these images, the machine determines whether an instrument among the set of instruments depicted in the first image was used or unused during the procedure (e.g., as part of performing the procedure) based on the first and second images. The machine then causes presentation of a notification that indicates whether the instrument was used or unused during the procedure.

FIG. 1 is a network diagram illustrating a network environment 100 suitable for operating an instrument tracking machine, according to some example embodiments. The network environment 100 includes a database 115 and devices 130 and 150 (e.g., as examples of instrument tracking machines), all communicatively coupled to each other via a network 190. The database 115 may form all or part of a cloud 118 (e.g., a geographically distributed set of multiple machines configured to function as a single server), which may form all or part of a network-based system 105 (e.g., a cloud-based server system configured to provide one or more network-based services to the devices 130 and 150). The database 115 and the devices 130 and 150 may each be implemented in a special-purpose (e.g., specialized) computer system, in whole or in part, as described below with respect to FIG. 11.

Also shown in FIG. 1 are users 132 and 152. One or both of the users 132 and 152 may be a human user (e.g., a human being, such as a nurse or a surgeon), a machine user (e.g., a computer configured by a software program to interact with the device 130 or 150), or any suitable combination thereof (e.g., a human assisted by a machine or a machine supervised by a human). The user 132 is associated with the device 130 and may be a user of the device 130. For example, the device 130 may be a desktop computer, a vehicle computer, a home media system (e.g., a home theater system or other home entertainment system), a tablet computer, a navigational device, a portable media device, a smart phone, or a wearable device (e.g., a smart watch, smart glasses, smart clothing, or smart jewelry) belonging to the user 132. Likewise, the user 152 is associated with the device 150 and may be a user of the device 150. As an example, the device 150 may be a desktop computer, a vehicle computer, a home media system (e.g., a home theater system or other home entertainment system), a tablet computer, a navigational device, a portable media device, a smart phone, or a wearable device (e.g., a smart watch, smart glasses, smart clothing, or smart jewelry) belonging to the user 152.

Any of the systems or machines (e.g., databases and devices) shown in FIG. 1 may be, include, or otherwise be implemented in a special-purpose (e.g., specialized or otherwise non-conventional and non-generic) computer that has been modified to perform one or more of the functions described herein for that system or machine (e.g., configured or programmed by special-purpose software, such as one or more software modules of a special-purpose application, operating system, firmware, middleware, or other software program). For example, a special-purpose computer system able to implement any one or more of the methodologies described herein is discussed below with respect to FIG. 11, and such a special-purpose computer may accordingly be a means for performing any one or more of the methodologies discussed herein. Within the technical field of such special-purpose computers, a special-purpose computer that has been specially modified (e.g, configured by special-purpose software) by the structures discussed herein to perform the functions discussed herein is technically improved compared to other special-purpose computers that lack the structures discussed herein or are otherwise unable to perform the functions discussed herein. Accordingly, a special-purpose machine configured according to the systems and methods discussed herein provides an improvement to the technology of similar special-purpose machines.

As used herein, a "database" is a data storage resource and may store data structured in any of various ways, for example, as a text file, a table, a spreadsheet, a relational database (e.g., an object-relational database), a triple store, a hierarchical data store, a document database, a graph database, key-value pairs, or any suitable combination thereof. Moreover, any two or more of the systems or machines illustrated in FIG. 1 may be combined into a single system or machine, and the functions described herein for any single system or machine may be subdivided among multiple systems or machines.

The network 190 may be any network that enables communication between or among systems, machines, databases, and devices (e.g., between the machine 110 and the device 130). Accordingly, the network 190 may be a wired network, a wireless network (e.g., a mobile or cellular network), or any suitable combination thereof. The network 190 may include one or more portions that constitute a private network, a public network (e.g., the Internet), or any suitable combination thereof. Accordingly, the network 190 may include one or more portions that incorporate a local area network (LAN), a wide area network (WAN), the Internet, a mobile telephone network (e.g., a cellular network), a wired telephone network (e.g., a plain old telephone service (POTS) network), a wireless data network (e.g., a WiFi network or WiMax network), or any suitable combination thereof. Any one or more portions of the network 190 may communicate information via a transmission medium. As used herein, "transmission medium" refers to any intangible (e.g., transitory) medium that is capable of communicating (e.g., transmitting) instructions for execution by a machine (e.g., by one or more processors of such a machine), and includes digital or analog communication signals or other intangible media to facilitate communication of such software.

Figure 2:
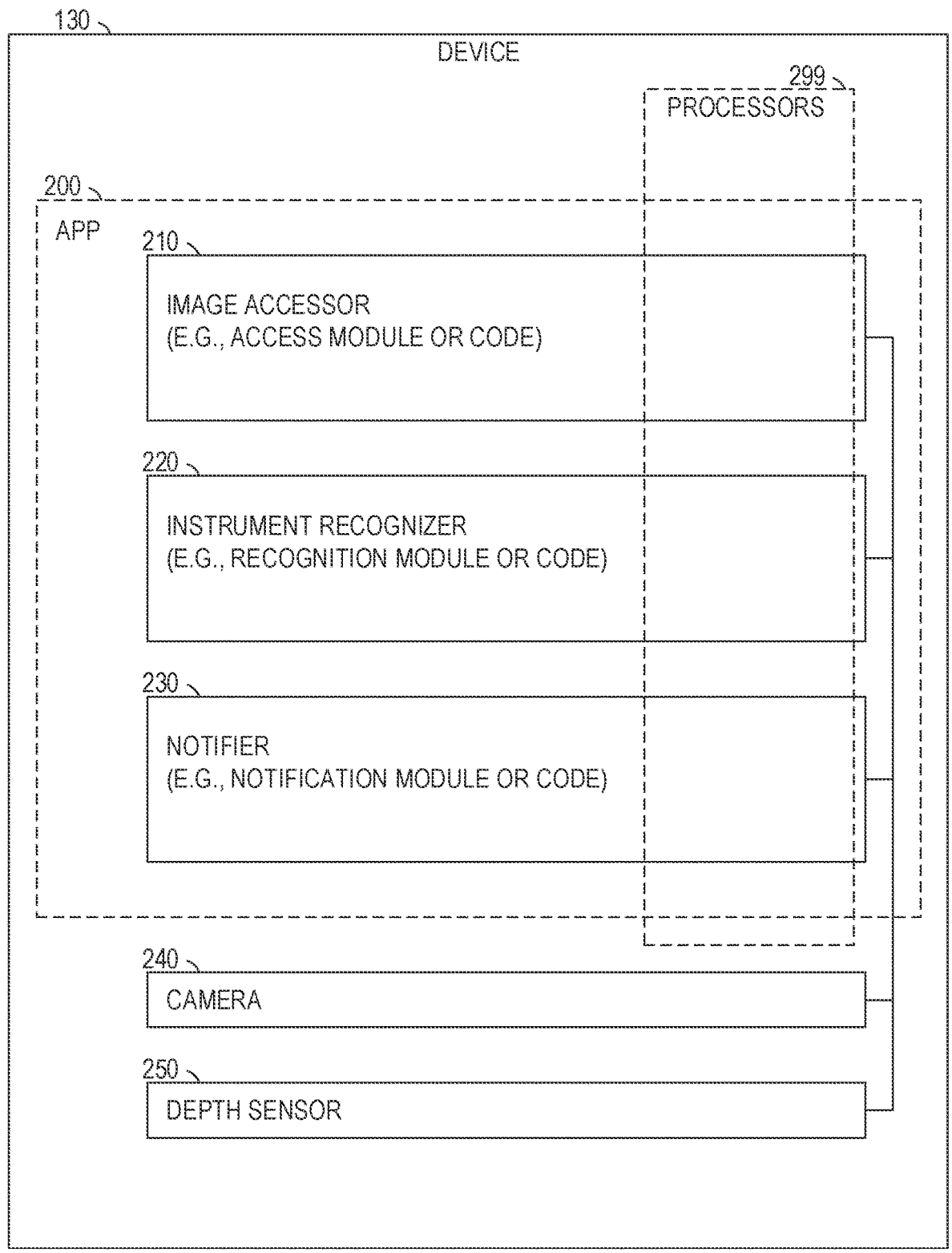
FIG. 2 is a block diagram illustrating components of a device a suitable for use as an instrument tracking machine, according to some example embodiments.

FIG. 2 is a block diagram illustrating components of the device 130, as configured to function as an instrument tracking machine, according to some example embodiments. The device 130 is shown as including an image accessor 210, an instrument recognizer 220, a notifier 230, a camera 240, and a depth sensor 250, all configured to communicate with each other (e.g., via a bus, shared memory, or a switch). The image accessor 210 may be or include an access module or similarly suitable software code for accessing one or more images. The instrument recognizer 220 may be or include a recognition module or similarly suitable software code for recognizing instruments (e.g., by type or as specific individual instances). The notifier 230 may be or include a notification module or similarly suitable software code for generating notifications and causing their presentation (e.g., on a display screen of the device 130, via an audio speaker of the device 130, or both).

The camera 240 may be or include an image capture component configured to capture one or more images (e.g., digital photos), and the captured images may include or may visualize optical data (e.g., RGB data or optical data in another colorspace), infrared data, ultraviolet data, ultrasonic data, radar data, or any suitable combination thereof. According to various example embodiments, the camera 240 may be on the back of a handheld phone, the front of a mounted device that includes a display screen, a set of one or more cameras mounted and aimed at a surgical tray, at a scrub technician's table (e.g., in an operating room), or at an assembly workstation (e.g., in an assembly room of an instrument supplier), or any suitable combination thereof. A set of cameras or the device 130 may be configured by the app 200 to fuse data from multiple cameras that are imaging a tray, a surface, or a/table (e.g., stereoscopically). In some situations, the device 130 is configured by the app 200 to access multiple images captured during motion (e.g., via image stitching) prior to processing, apply a structure-from-motion algorithm, or both, to support or enhance instrument detection, instrument classification, instrument identification, or any suitable combination thereof, as discussed elsewhere herein.

The depth sensor 250 may be or include an infrared sensor, a radar sensor, an ultrasound sensor, an optical sensor, a time-of-flight camera, a structured light scanner, or any suitable combination thereof. Accordingly, the depth sensor 250 may be configured to generate depth data corresponding to (e.g., representing distances to) one or more objects (e.g., instruments) within range of the depth sensor 250 (e.g., within range in a field of view or in a field of detection).

As shown in FIG. 2, the image accessor 210, the instrument recognizer 220, the notifier 230, or any suitable combination thereof, may form all or part of an app 200 (e.g., a mobile app) that is stored (e.g., installed) on the device 130 (e.g., responsive to or otherwise as a result of data being received from the device 130 via the network 190) and executable thereon. Furthermore, one or more processors 299 (e.g., hardware processors, digital processors, or any suitable combination thereof) may be included (e.g., temporarily or permanently) in the app 200, the image accessor 210, the instrument recognizer 220, the notifier 230, or any suitable combination thereof.

Any one or more of the components (e.g., modules) described herein may be implemented using hardware alone (e.g., one or more of the processors 299) or a combination of hardware and software. For example, any component described herein may physically include an arrangement of one or more of the processors 299 (e.g., a subset of or among the processors 299) configured to perform the operations described herein for that component. As another example, any component described herein may include software, hardware, or both, that configure an arrangement of one or more of the processors 299 to perform the operations described herein for that component. Accordingly, different components described herein may include and configure different arrangements of the processors 299 at different points in time or a single arrangement of the processors 299 at different points in time. Each component (e.g., module) described herein is an example of a means for performing the operations described herein for that component. Moreover, any two or more components described herein may be combined into a single component, and the functions described herein for a single component may be subdivided among multiple components. Furthermore, according to various example embodiments, components described herein as being implemented within a single system or machine (e.g., a single device) may be distributed across multiple systems or machines (e.g., multiple devices).

Figure 3:
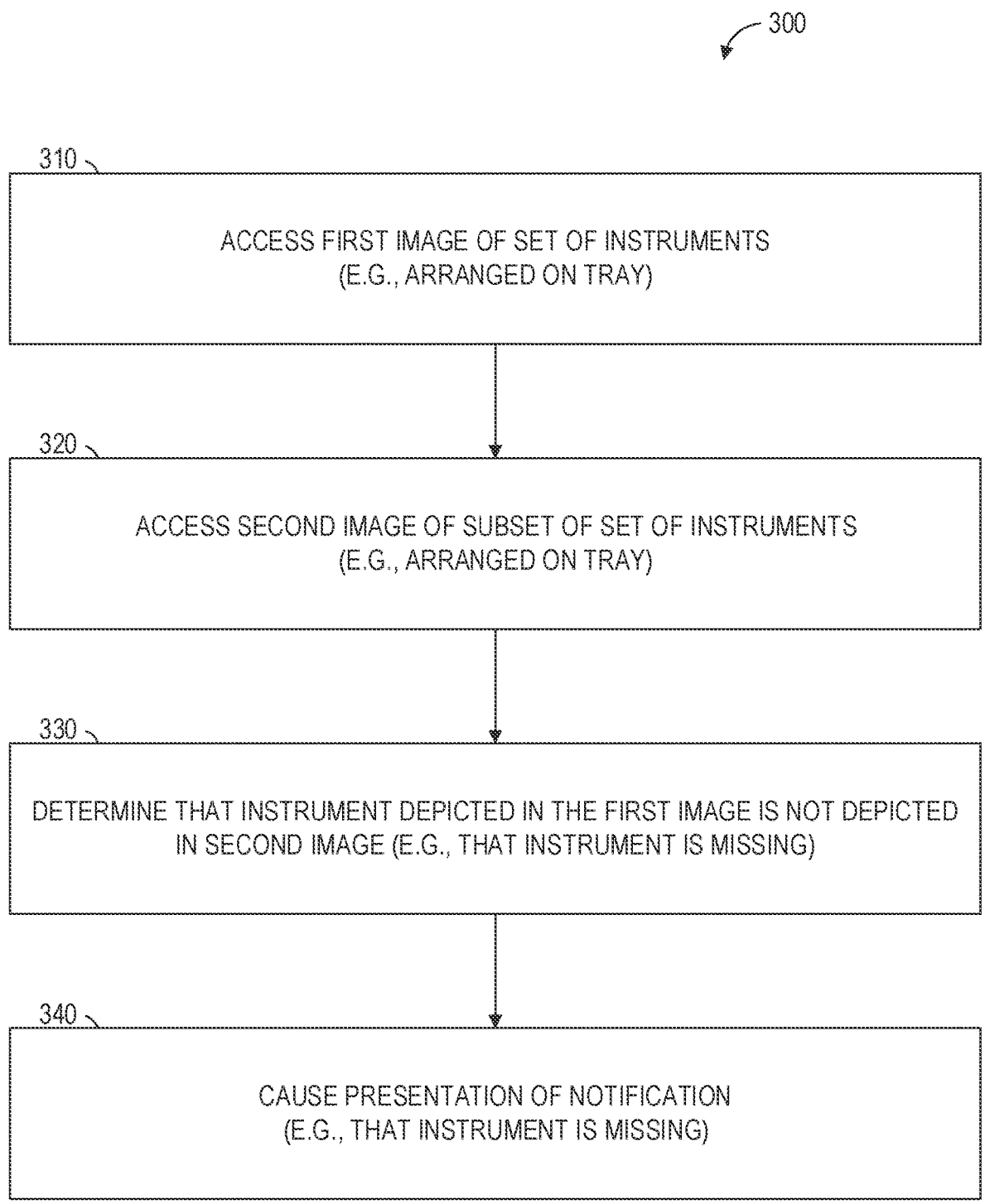
FIGS. 3 and 4 are flowcharts illustrating operations of the device in performing a method of tracking instruments, according to some example embodiments.
Figure 4:
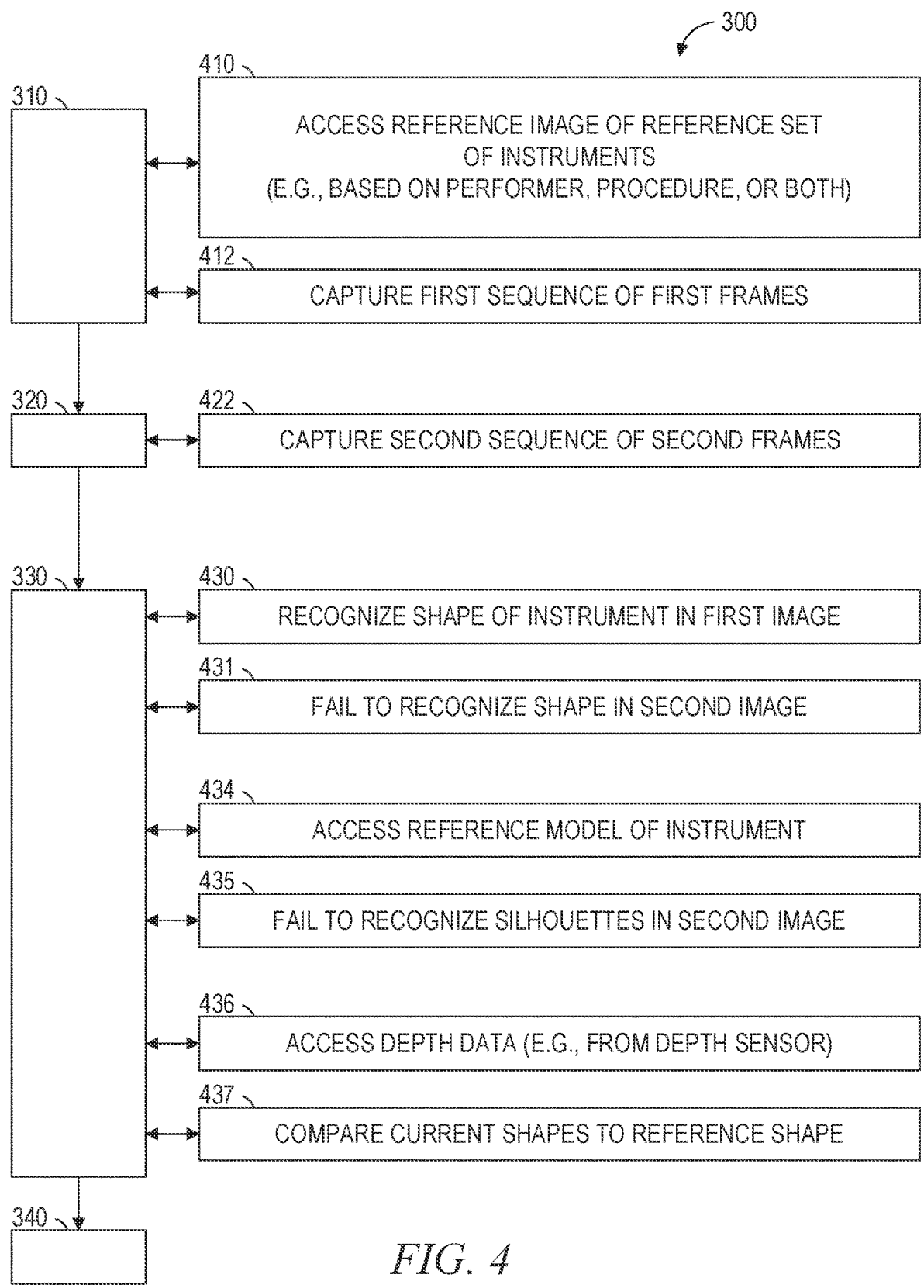

FIGS. 3 and 4 are flowcharts illustrating operations of the device 130 in performing a method 300 of tracking instruments, according to some example embodiments. Operations in the method 300 may be performed by the device 130, using components (e.g., modules) described above with respect to FIG. 2, using one or more processors (e.g., microprocessors or other hardware processors), or using any suitable combination thereof. As shown in FIG. 3, the method 300 includes operations 310, 320, 330, and 340.

In operation 310, the image accessor 210 accesses (e.g., receives, retrieves, reads, or otherwise obtains) a first image that was captured prior to initiation of a procedure. The first image depicts a set of instruments (e.g., a reference set of instruments) available for use in performing the procedure. For example, the first image may be captured by the camera 240 of the device 130 (e.g., by taking a digital photograph of a surgical tray in which a set of surgical instruments has been arranged in preparation for a surgical procedure to be performed by surgeon). In some example embodiments, the first image is accessed by the image accessor 210 from the database 115 via the network 190. One or more fiducial markers may also be depicted in the first image, and such fiducial markers may be a basis for increasing effectiveness of instrument classification, instrument identification, or both, to be performed in operation 330.

In operation 320, the image accessor 210 accesses a second image that was captured after initiation of the procedure (e.g., midway during the procedure, just before completion of the procedure, or after completion of the procedure). The second image depicts a proper subset (e.g., a portion) of the set of instruments depicted in the first image. For example, the second image may be captured by the camera 240 of the device 130 (e.g., by taking a digital photograph of the surgical tray in which a portion of the set of instruments depicted in the first image has been arranged after initiation of the surgical procedure and before the surgeon closes up the patient on which the surgical procedure is performed). In some example embodiments, the second image is accessed by the image accessor 210 from the database 115 via the network 190. One or more fiducial markers may also be depicted in the second image, and such fiducial markers may be a basis for increasing effectiveness of instrument classification, instrument identification, or both, to be performed in operation 330.

In operation 330, the instrument recognizer 220 determines that an instrument among the set of instruments depicted in the first image is not depicted among the proper subset of the set of instruments in the second image. According to some example embodiments, the instrument recognizer 220 performs instrument classification to determine that a non-specific instance of a certain type of instrument is missing from the second image (e.g., that one of seven forceps is missing because seven forceps are depicted in the first image, while only six forceps are depicted in the second image). According to certain example embodiments, the instrument recognizer 220 performs instrument identification to determine that a specific individual instrument is missing from the second image (e.g., that a particular scissors is depicted in the first image but not in the second image). In hybrid example embodiments, the instrument recognizer 220 performs both instrument identification and instrument classification. In further example embodiments, such as when counts of discrete instruments cannot be made with a minimum threshold confidence value, the instrument recognizer 220 performs aggregated instrument detection and aggregated instrument classification to determine that an aggregate of instruments having a shared type (e.g., a stack of clamps) has changed (e.g., decreased) in volume, area, height, or other indicator of size from the first image to the second image.

For performing instrument classification, the instrument recognizer 220 may be or include an artificial intelligence module (e.g., an artificially intelligent machine-learning module trained to implement one or more computer vision algorithms) in the form of an instrument classifier trained to detect and classify instruments depicted in images (e.g., an image depicting surgical instruments arranged within an instrument tray), for example, using real-time computer vision techniques. The instrument classifier may be or include a deep convolutional neural network, such as one with several convolutional layers. The deep convolutional neural network may have an activation layer (e.g., a Softmax activation layer) at the top, and there may be N outputs to predict the probability of N different types (e.g., categories) of instruments. Accordingly, the instrument type that corresponds to the highest probability may be selected by the instrument classifier as the predicted type of the instrument depicted.

In some example embodiments, the instrument classifier in the instrument recognizer 220 is trained (e.g., by a trainer machine) based on a classification training model that has multiple convolutional layers was increasing filter sizes. For example, there may be 4 convolutional layers with increasing filter sizes from 8 to 32, with rectified learning units as their activation functions, which may be followed by a batch norm layer, a pooling layer, or both. Accordingly, the fully connected layer may include 14 nodes that represent 14 types (e.g., categories) of instruments in a training set, along with Softmax activation. The classification training model may use an adaptive learning rate optimization algorithm (e.g., Adam), and may use categorical cross-entropy as a loss function.

According to certain example embodiments, the training set may contain (e.g., exclusively or non-exclusively) reference images that depict reference sets of instruments, and such reference sets may be customized for specific procedures, surgeons, hospitals, instrument suppliers, geographical regions, or any suitable combination thereof. Moreover, the training set may include reference images captured under a variety of lighting conditions, reference images with corresponding three-dimensional data (e.g., depth data or a model of a depicted instrument), reference images of reference conveyances (e.g., reference trays, which may be empty or populated with instruments), reference images of background items (e.g., towel, drapes, floor surfaces, or table surfaces), or any suitable combination thereof.

For performing instrument identification, the instrument recognizer 220 may be or include an artificial intelligence module in the form of an object identifier trained to locate and identify objects of interest within a given image (e.g., by drawing bounding boxes around located instruments and analyzing the contents inside the bounding boxes). For example, the object identifier may be or include a single shot detector (SSD) with inception-V2 as the feature extractor. However, other variants of neural network architecture may be suitable, as well as other classes of neural networks suitable for detection, classification, or identification of objects, to balance trade-offs between accuracy and inference time. An example training dataset may include N (e.g., N=10) different types (e.g., categories) for instruments and a few hundred to a few thousand images (e.g., 227 images or 5000 images). The object identifier may evaluate bounding box metrics using Pascal VOC metrics.

In certain example embodiments, the object identifier in the instrument recognizer 220 is trained using a large synthetic dataset (e.g., to avoid problems with using a dataset that is too small). An example training procedure starts by a trainer machine (e.g., controlling a renderer machine or functioning as a renderer machine) physically simulating a three-dimensional (3D) scene, as well as simulating the parameter of a known camera. Then, the trainer machine randomly places 3D objects in the scene (e.g., randomly places 3D instruments onto a 3D tray) and renders the scene based on various factors, such as object occlusion, lighting, shadows, etc. The trainer machine then artificially captures images of the rendered 3D objects in the scene. The system randomly changes (e.g., via domain randomization) the location, orientation or pose of the 3D objects, the lighting, the camera-location, and the number of 3D objects in this simulation to automatically generate a large and diverse synthetic dataset of images. Appropriate corresponding data labels (e.g. the bounding box and the segmentation mask) may be automatically generated by the trainer machine during the simulation, thereby reducing labeling cost.

According to some example embodiments, the trainer machine trains the object identifier in the instrument recognizer 220 in the following manner. First, the trainer machine pre-trains the object identifier (e.g., trains the object identification model implemented by the object identifier) using a synthetically generated dataset of images depicting surgical instruments. After pre-training with this synthetic dataset, the trainer machine modifies (e.g., by further training) the object identifier based on a small real (e.g., non-synthetic) dataset of images depicting specific types of surgical instruments. The small real dataset may be human-curated. In certain example embodiments, a suitable alternative to the trainer machine performs the training of the object identifier.

Step 1: To generate the synthetic surgical instrument dataset, the trainer machine may launch or otherwise invoke one or more rendering applications (e.g., Blender" or Unreal Gaming Engine"). For rendering synthetic images, the trainer machine may access the following example inputs:
1. 3D models (e.g., computer-aided design (CAD) models) of different surgical instruments,
2. surface texture information for the surgical instruments,
3. ranges of parameters for defining lighting (e.g., to simulate a hospital operating room), such as the brightness range or the ranges of spectral composition variations,
4. ranges of possible camera locations relative to the surgical trays on which the surgical instruments are to be placed (e.g., azimuth, elevation, pan, tilt, etc.) to capture images from specific angles, and
5. the number and types of instruments to be rendered.

In certain example embodiments, the trainer machine artificially places a random number of virtual surgical instruments on a virtual surgical tray with arbitrary orientations and positions. The trainer machine then generates synthetic images that exhibit different amounts of occlusions, ranging from no occlusion to severe occlusion. The amount of occlusion in the synthetic dataset can be a customized parameter during this simulation.

Step 2: The trainer machine trains the object identifier by using the synthetic surgical instrument dataset generated in Step 1 as the training dataset.

Step 3: The trainer machine accesses (e.g., from the database 115) a small dataset of realistic images depicting real surgical instruments placed naturally on a real surgical tray. The dataset of realistic images helps bridge the difference between using synthesized images and using real images (e.g., between training the object identifier exclusively with a large number of synthesized images and training the object identifier exclusively with a small number of real images).

In some implementations, one or more fiducial markers on a conveyance for the instruments (e.g., on a surgical tray) or on the instruments themselves can be used to aid in instrument detection, instrument classification, instrument identification, or any suitable combination thereof. For example, where the conveyance is a specialized orthopedic tray, the instrument recognizer 220 may access a template image (e.g., a mask image) that depicts an empty orthopedic tray without any instruments, and then subtract the template image from the first image to obtain a first differential image (e.g., a first segmentation image) that more clearly depicts the individual instruments prior to initiation of the procedure. Similarly, the instrument recognizer 220 may subtract the template image from the second image to obtain a second differential image (e.g., a second segmentation image) that more clearly depicts the individual instruments after initiation of the procedure (e.g., at or near the end of the procedure). The first and second differential images may be prepared by the instrument recognizer 220 in preparation for operation 340 or for alternative implementations of instrument detection, instrument classification, instrument identification, or any suitable combination thereof. In this sense, the orthopedic tray acts as a fiducial marker in the first image, the second image, or both.

In certain example embodiments, the outputs of multiple independent classifiers (e.g., deep learning classifiers, differential image classifiers, or any suitable combinations thereof) are combined to improve accuracy, precision, or both, in performing instrument classification, instrument identification, or both, with respect to a given conveyance (e.g., a tray) of instruments. Specifically, independent algorithms can determine and output corresponding probabilities indicating (1) whether a tray is complete or incomplete, (2) whether each predetermined template region among multiple predetermined template regions of the tray is filled or not filled, and (3) what is the classification of each object detected on the tray (e.g., whether it an instrument, and if so, what type of instrument). The union of these three independent algorithms may better represent whether the tray is indeed complete, and if so which instrument is likely missing.

In operation 340, the notifier 230 causes presentation (e.g., visual, auditory, or both) of a notification that indicates that the instrument not depicted in the second image is missing from the set of instruments. The presentation of the notification may take the example form of displaying a pop-up window, playing an alert sound, sending a message to a further device (e.g., a smartphone of the nurse or of the surgeon), triggering a predetermined procedure that corresponds to instruments being deemed as missing (e.g., an instrument finding procedure or a patient check procedure), or any suitable combination thereof.

According to various example embodiments, the presented notification indicates whether a specific instrument is missing. Alternatively, or in addition, the presented notification may indicate whether a conveyance (e.g., a tray or a cart) for the set of instruments depicted in the first image is complete or incomplete (e.g., compared to a reference set of instruments, such as a standard surgical tray of instruments, a closing tray of instruments, or an orthopedic tray of instruments). Alternatively, or in addition, the presented notification may include a standardized report that lists each instrument in the set of instruments depicted in the first image, along with corresponding indicators (e.g., a marker or a flag) of whether that instrument was used or not, when the instrument was picked up (e.g., as a timestamp), when the instrument was returned (e.g., to the scrub tech or to the conveyance), the residence time of the instrument in the body of the patient, whether the instrument ever came out or is still retained, or any suitable combination thereof. In some example embodiments, the presented notification includes a total count of missing instruments, a list of missing instruments (e.g., denoted by type, denoted as specific individual instruments, or both), or any suitable combination thereof.

Furthermore, a user feedback feature may be implemented by the app 200, such that the user 132 is prompted to confirm or correct a presented total count of present or absent instruments, and the response of the user 132 is used as labels to further train and improve one or more artificial intelligence modules in the instrument recognizer 220. In some example embodiments, the app 200 can operate with more user interaction and prompt the user 132 to confirm (e.g., manually, visually, or both) some or all of the information contained in the presented notification.

As shown in FIG. 4, in addition to any one or more of the operations previously described for the method 300, the method 300 may include one or more of operations 410, 412, 422, 430, 431, 434, 435, 436, and 437.

Operation 410 may be performed as part (e.g., a precursor task, a subroutine, or a portion) of operation 310, in which the image accessor 210 accesses the first image. In operation 410, the first image is a reference image that depicts a reference set of instruments (e.g., a standardized set of instruments) that correspond to the procedure (e.g., by virtue of being designated for the procedure), to a performer (e.g., a surgeon) of the procedure (e.g., by virtue of being designated by the performer), or to both, and the reference image is accessed based on (e.g., in response to) its correspondence to the procedure, to the performer of the procedure, or to both.

In alternative example embodiments, operation 412 may be performed as part of operation 310. In operation 412, the first image is accessed by capturing the first image as part of capturing a sequence of frames (e.g., a first sequence of first frames of video). For example, the image accessor 210 may access video data from the camera 240 while the device 130 is moved over the set of instruments (e.g., passed over a surgical tray holding the set of instruments) and record a sequence of video frames, among which is the first image. In such example embodiments, the app 200 may include and execute a stereoscopic algorithm (e.g., a structure-from-motion algorithm) configured to infer depth data from the sequence of video frames that includes the first image, and this depth data may be a basis or other factor in the determination, in operation 330, that the instrument is missing.

Similarly, in certain example embodiments, operation 422 may be performed as part of operation 320, in which the image accessor 210 accesses the second image. In operation 422, the second image is accessed by capturing the second image as part of capturing a sequence of frames (e.g., a second sequence of second frames of video). For example, the image accessor 210 may access video data from the camera 240 while the device 130 is moved over the portion of the set of instruments (e.g., passed over the surgical tray holding the portion of the set of instruments) and record a sequence of video frames, among which is the second image. In such example embodiments, the app 200 may include and execute a stereoscopic algorithm configured to infer depth data from the sequence of video frames that includes the second image, and this depth data may be a basis or other factor in the determination, in operation 330, that the instrument is missing.

As shown in FIG. 4, operations 430 and 431 may be performed as part of operation 330, in which the instrument recognizer 220 determines that the instrument among the set of instruments depicted in the first image is not depicted among the proper subset of the set of instruments in the second image.

In operation 430, the instrument recognizer 220 recognizes (e.g., optically, with or without supplemental support from depth data) a shape of the instrument in the first image. For example, as noted above, the instrument recognizer 220 may be or include an instrument classifier, an object identifier, or a combination of both, and the instrument recognizer 220 may accordingly be trained to detect (e.g., identify) and classify the instrument by its shape, as depicted in the first image.

In operation 431, the instrument recognizer 220 attempts but fails to recognize (e.g., optically, with or without supplemental support from depth data) the shape of the instrument in the second image. For example, as noted above, the instrument recognizer 220 may be or include an instrument classifier, an object identifier, or a combination of both, and the instrument recognizer 220 may accordingly be trained to detect (e.g., identify) and classify the instrument by its shape, as depicted in the second image. However, because the instrument is not depicted in the second image, the instrument recognizer 220 fails to detect or classify the instrument.

As shown in FIG. 4, operations 434 and 435 may be performed as part of operation 330, in which the instrument recognizer 220 determines that the instrument among the set of instruments depicted in the first image is not depicted among the proper subset of the set of instruments in the second image.

In operation 434, the instrument recognizer 220 accesses a reference model of the instrument. The reference model may be three-dimensional and may be accessed from the database 115. For example, if operation 430 has been performed, the instrument recognizer 220 may access the reference model of the instrument based on (e.g., in response to) the identifying of the instrument by its shape in operation 430.

In operation 435, the instrument recognizer 220 attempts but fails to recognize (e.g., optically, with or without supplemental support from depth data), in the second image, each of a plurality of silhouettes of the reference model of the instrument (e.g., as accessed in operation 434). For example, the instrument recognizer 220 may generate a set of silhouettes from the reference model and compare each silhouette in the set of silhouettes to shapes of the instruments in the proper subset of the set of instruments, as depicted in the second image. However, because the instrument is not depicted in the second image, the instrument recognizer 220 fails to recognize any of the silhouettes of the reference model of the instrument in the second image.

As shown in FIG. 4, operations 436 and 437 may be performed as part of operation 330, in which the instrument recognizer 220 determines that the instrument among the set of instruments depicted in the first image is not depicted among the proper subset of the set of instruments in the second image.

In operation 436, the instrument recognizer 220 accesses depth data that represents current shapes of the proper subset of the set of instruments depicted in the second image. For example, the depth data may be captured by the depth sensor 250 of the device 130, and the instrument recognizer 220 may access the depth data from the depth sensor 250.

In operation 437, the instrument recognizer 220 compares the reference shape of the instrument to each of current shapes of the proper subset of the set of instruments. As noted above, the current shapes may be represented by the depth data accessed in operation 436. If operation 434 has been previously performed to access the reference model that represents the reference shape of the instrument, the same reference shape may be used in the comparison performed here in operation 437. In other example embodiments, operation 437 includes accessing or otherwise obtaining the reference shape of the instrument (e.g., in a manner similar to that described above for operation 434.

Figure 5:
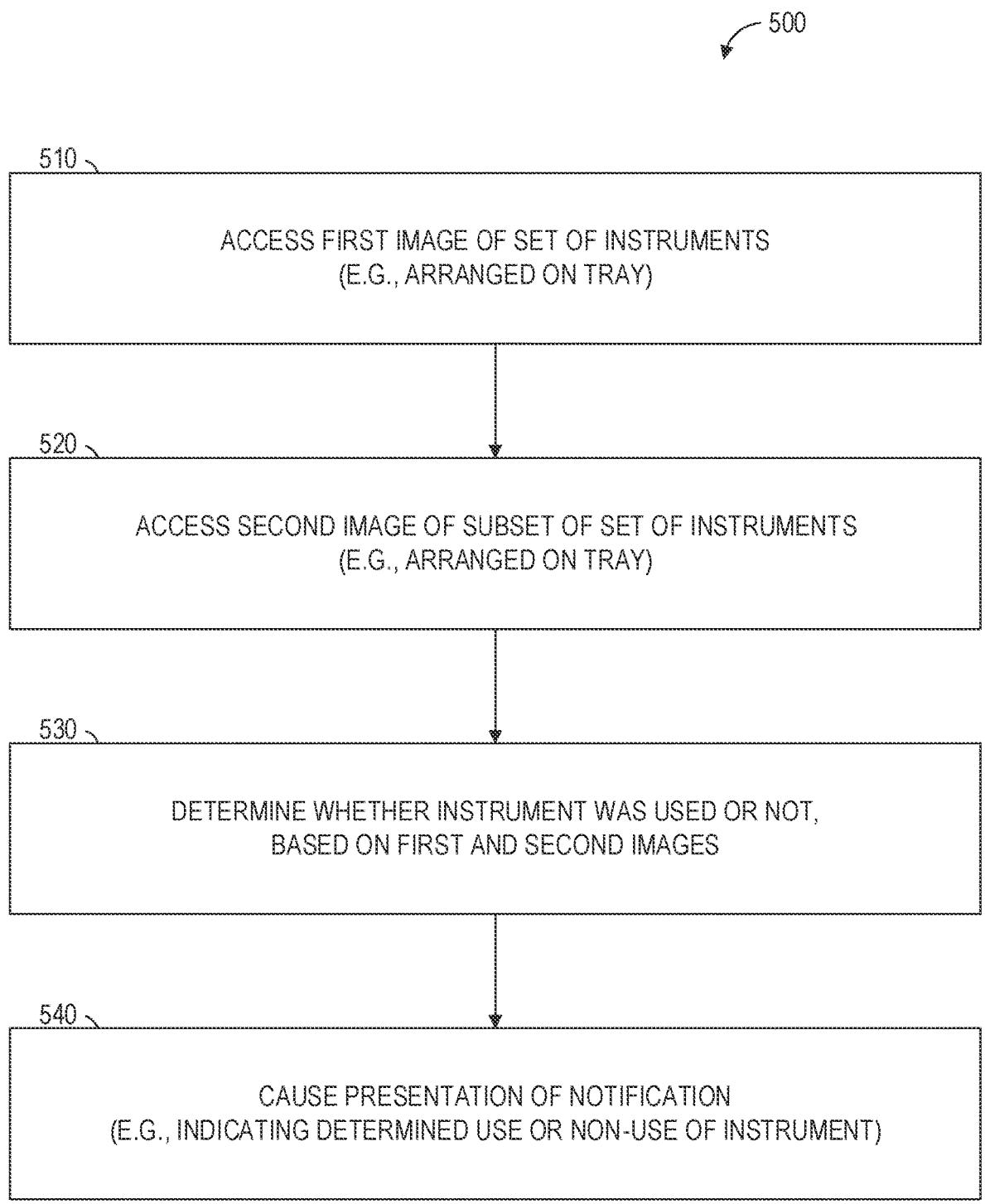
FIGS. 5 and 6 are flowcharts illustrating operations of the device in performing another method of tracking instruments, according to some example embodiments.
Figure 6:
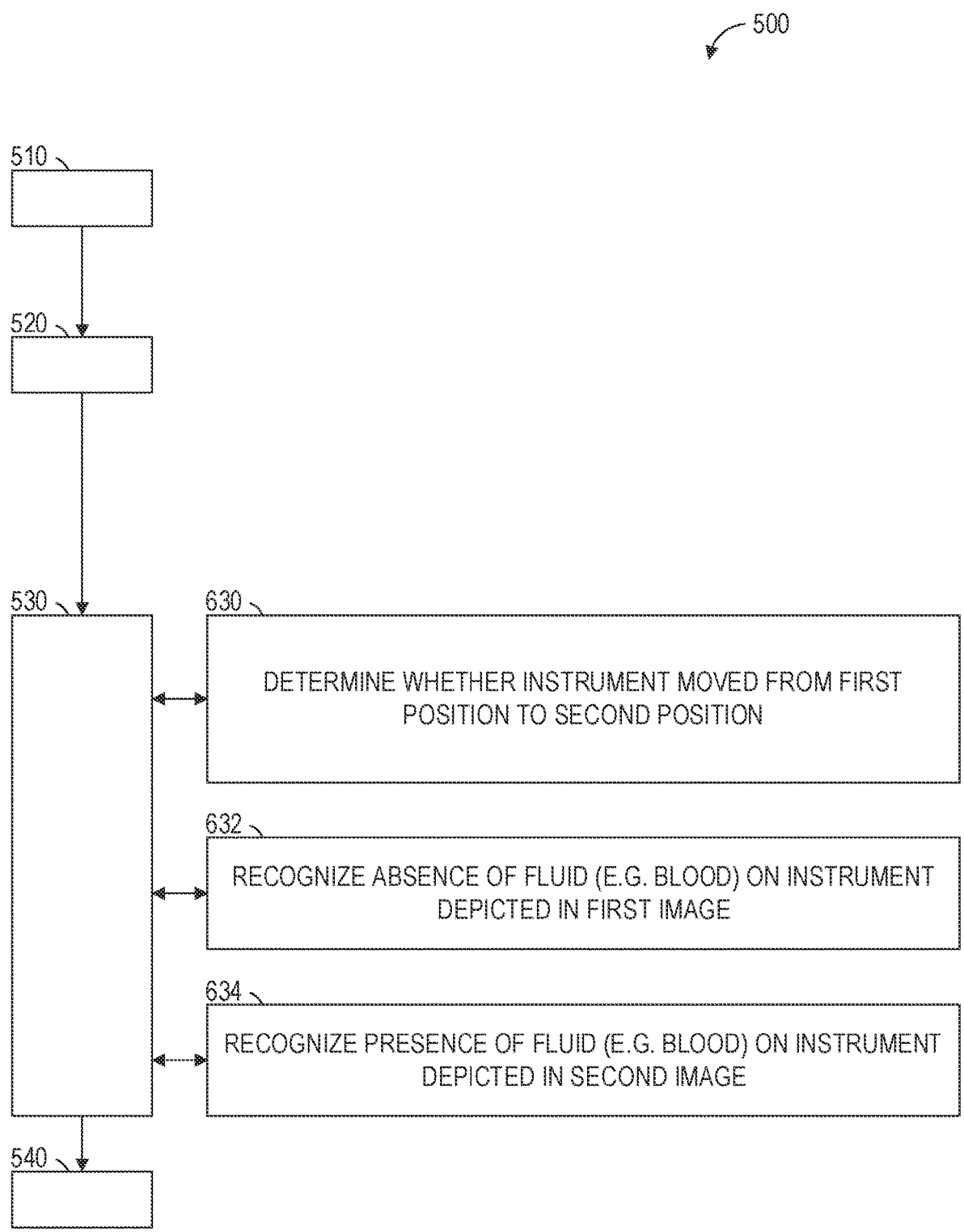

FIGS. 5 and 6 are flowcharts illustrating operations of the device 130 in performing a method 500 of tracking instruments, according to some example embodiments. Operations in the method 500 may be performed by the device 130, using components (e.g., modules) described above with respect to FIG. 2, using one or more processors (e.g., microprocessors or other hardware processors), or using any suitable combination thereof. As shown in FIG. 5, the method 500 includes operations 510, 520, 530, and 540.

In operation 510, the image accessor 210 accesses (e.g., receives, retrieves, reads, or otherwise obtains) a first image that was captured prior to initiation of a procedure. The first image depicts a set of instruments available for use in performing the procedure. For example, the first image may be captured by the camera 240 of the device 130 (e.g., by taking a digital photograph of a surgical tray in which a set of surgical instruments has been arranged in preparation for a surgical procedure to be performed by surgeon). In some example embodiments, the first image is accessed by the image accessor 210 from the database 115 via the network 190. One or more fiducial markers may also be depicted in the first image, and such fiducial markers may be a basis for increasing effectiveness of instrument identification to be performed in operation 530. In various example embodiments, operation 510 is performed similarly to operation 310 in the method 300, as described above.

In operation 520, the image accessor 210 accesses a second image that was captured after initiation of the procedure. The second image depicts a subset of the set of instruments depicted in the first image. The subset may be a proper subset (e.g., a portion) of the set of instruments or a subset that coincides with the entire set of instruments. That is, there may be no instruments missing in the second image. For example, the second image may be captured by the camera 240 of the device 130 (e.g., by taking a digital photograph of the surgical tray in which a portion of the set of instruments depicted in the first image has been arranged after initiation of the surgical procedure and before the surgeon closes up the patient on which the surgical procedure is performed). In some example embodiments, the second image is accessed by the image accessor 210 from the database 115 via the network 190. One or more fiducial markers may also be depicted in the second image, and such fiducial markers may be a basis for increasing effectiveness of instrument identification to be performed in operation 530.

In operation 530, the instrument recognizer 220 determines whether an instrument among the set of instruments depicted in the first image was used or unused in the procedure, based on the first and second images. According to some example embodiments, the instrument recognizer 220 performs instrument identification to determine that a specific individual instrument is present in both images but exhibiting one or more optically detectable indications of usage. Such indications include, for example, movement from a first location within a conveyance (e.g, a surgical tray) in the first image to a second location within the conveyance in the second image, a change in appearance from having an absence of a bioburden (e.g., one or more spots of a patient fluid, such as blood) in the first image to having a presence of the bioburden in the second image, or any suitable combination thereof. Example details of algorithms used by the instrument recognizer 220 in performing instrument identification (e.g., via an object identifier) and example details of training the instrument recognizer 220 (e.g., the object identifier) are discussed above (e.g., with respect to operation 330 in the method 300). For example, one or more fiducial markers may be used in the first image, the second image, or both, in a manner similar to that described above.

In operation 540, the notifier 230 causes presentation (e.g., visual, auditory, or both) of a notification that indicates whether the instrument was used or unused in the procedure. The presentation of the notification may take the example form of displaying a pop-up window, playing an alert sound, sending a message to a further device (e.g., a smartphone of the nurse, the surgeon, an orderly, or an inventory manager), triggering a predetermined procedure that corresponds to the used or unused state determined for the instrument (e.g., a used instrument counting procedure, an unused instrument counting procedure, or an instrument sterilization procedure), or any suitable combination thereof.

Furthermore, in certain example embodiments, operations 510 and 530 may be performed without one or both of operations 520 and 540, such that an instrument depicted in the first image is directly classified, identified, or both, with a resultant presentation of a notification that indicates a count of instruments classified, identified, or both; the type of the instrument, a name of the instrument, a reference image of the instrument, or any suitable combination thereof. Such example embodiments may be helpful in situations where a new scrub technician or a new surgeon is unable to recall or does not know what an instrument is called. To quickly classify or identify the instrument by machine, the new scrub technician or the new surgeon can hold an instrument in front of the camera 240 of the device 130, and the app 200 can use computer vision and deep learning (e.g., by performing the instrument classification, instrument identification, or both, as described above with respect to operation 330) to obtain an answer, which may be provided a likelihood score indicating a level of confidence in the answer. Some of these example embodiments are situated in a mounted supply chain setting, where a camera (e.g., the camera 240) is positioned to image a table, an instrument tray assembler places an instrument on the table, and a device (e.g., the device 130, as described herein) scans the instrument and performs automatic classification, identification, or both, on the scanned instrument.

Yet furthermore, in various example embodiments, operations 510 and 530 may be performed without one or both of operations 520 and 540, such that improvements to supply chain efficiency are obtained by replacing one or more highly manual processes (e.g., manually marking off a standardized electronic checklist as instruments are manually added to a new tray) with an automated checklist based on the systems and methods discussed herein. In such example embodiments, a tray assembler can grab an instrument, image the instrument (e.g., using one or more of many modalities), and a device (e.g., the device 130) automatically checks off that instrument on an assembly sheet (e.g., listing instruments to be added to a new tray).

Still furthermore, in some example embodiments, operations 510 and 530 are repeatedly performed, such that a visual record is generated to track, for example, whether or when each instrument is removed from a tray, whether or when each removed instrument was returned to the tray, and whether each removed instrument looks used or not. All or part of such a visual record may be provided (e.g., by the device 130 to the database 115) for inclusion in an electronic medical record (e.g., corresponding to the patient undergoing the procedure)

Moreover, the automatic classification or identification of instruments discussed herein can extend beyond instruments on trays to provide similar benefits for any other consumable items found in hospital operating rooms, and onward to other settings as well. For example, medications in a medication cart can be tracked in a manner similar to that described herein for instruments on a tray (e.g., to ensure that controlled substances, such as opioids, are not misused or lost during a surgery). Accordingly, in some example embodiments, medications can be scanned by a device (e.g., the device 130) configured by an app (e.g., app 200), and when each medication is used by an anesthesiologist, the device may cause presentation of a notification that indicates all or part of a visual record for the medicine cart. The visual record may indicate how each medication (e.g., each controlled substance) was administered or otherwise used, along with corresponding timestamps of administration or other usage.

As shown in FIG. 6, in addition to any one or more of the operations previously described for the method 500, the method 500 may include one or more of operations 630, 632, and 634. One or more of operations 630, 632, and 634 may be performed as part of operation 630, in which the instrument recognizer 220 determines whether the instrument depicted in the first image was used or unused in the procedure, based on the first and second images.

In operation 630, as part of determining whether the instrument was used or not, the instrument recognizer 220 determines whether the instrument moved from a first position within a conveyance depicted in the first image to a second position within the conveyance depicted in the second image.

In operation 632, as part of determining whether the instrument was used or not, the instrument recognizer 220 recognizes (e.g., optically) an absence of a bioburden (e.g., a bloodstain or a spot of other bodily fluid from a patient) on the instrument depicted in the first image.

In operation 634, as part of determining whether the instrument was used or not, the instrument recognizer 220 recognizes (e.g., optically) a presence of the bioburden (e.g., one or more bloodstains or spots of another bodily fluid from the patient) on the same instrument, as depicted in the second image.

According to various example embodiments, one or more of the methodologies described herein may facilitate tracking of instruments (e.g., surgical instruments). Moreover, one or more of the methodologies described herein may facilitate detection and quantification of instruments by type, detection and tracking of individual instruments, or both. Hence, one or more of the methodologies described herein may facilitate more precise and accurate management of instrument inventories and the associated costs for their maintenance (e.g., sterilization procedures), as well as reduction of risks to health and safety (e.g., of patients who undergo medical procedures), compared to capabilities of pre-existing systems and methods.

Figure 7:
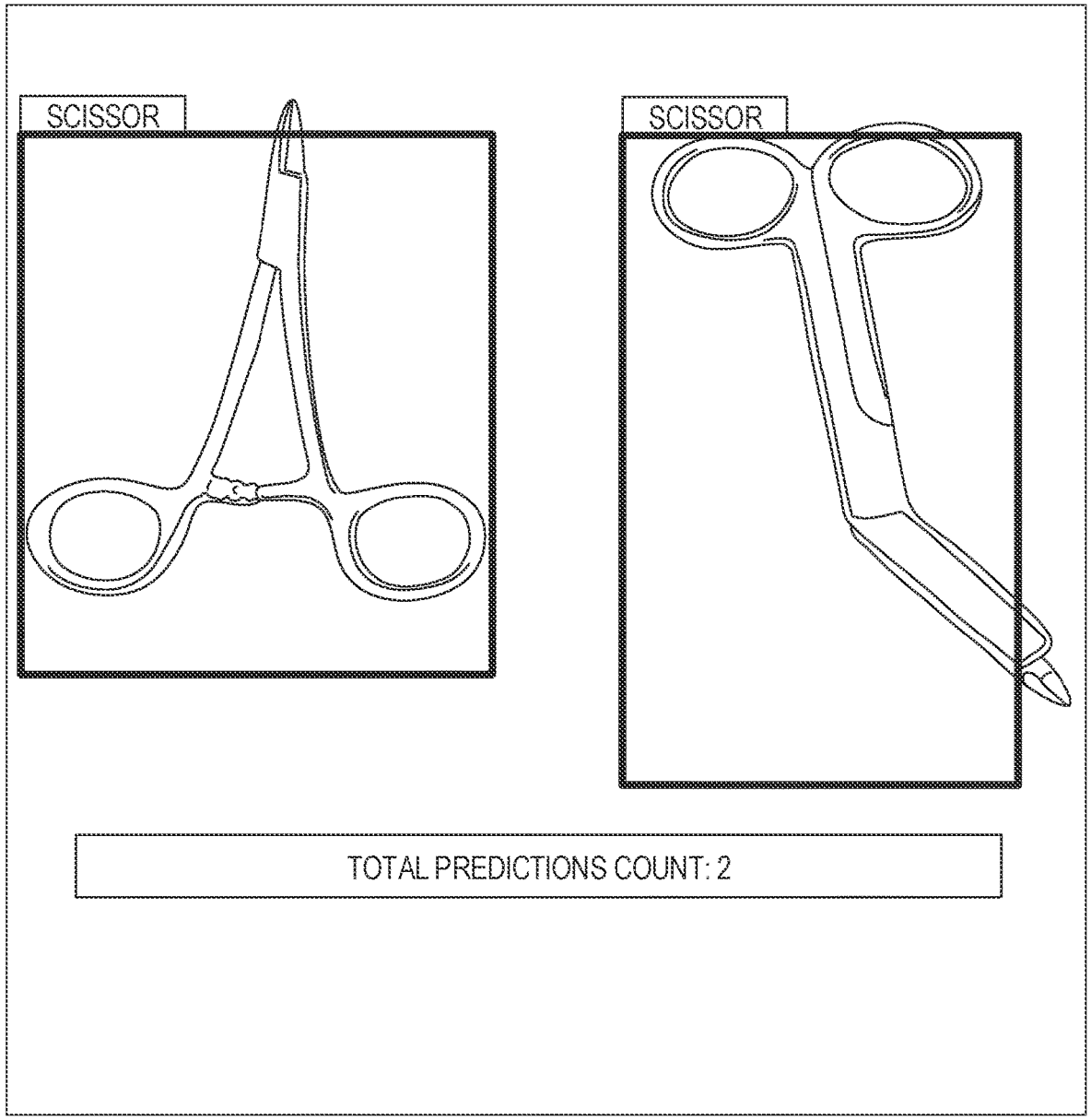
FIG. 7 is a screenshot illustrating an image that depicts instruments and in which a device configured by an app has added bounding boxes that indicate the instruments, according to some example embodiments.

FIG. 7 is a screenshot illustrating an image that depicts instruments and in which the device 130 configured by the app 200 has added bounding boxes that indicate the instruments, according to some example embodiments.

Figure 8:
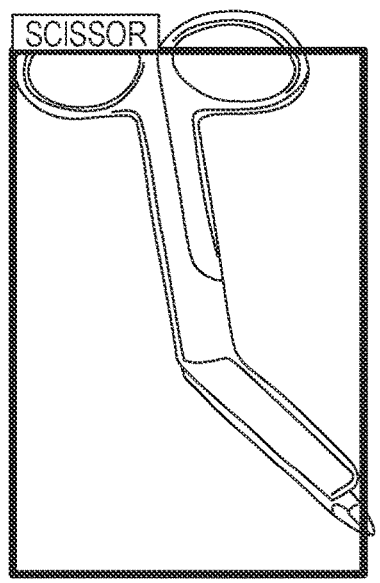
FIGS. 8-10 are screenshots illustrating images that depict instruments and in which the device configured by the app, for each image, has added counts of the instruments both individually and by type of instrument, according to some example embodiments.
Figure 8:
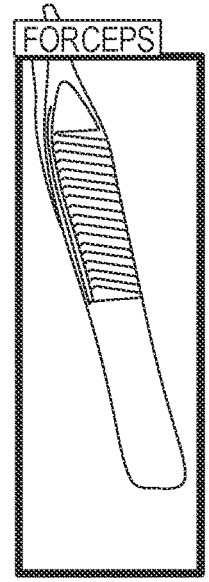
Figure 9:
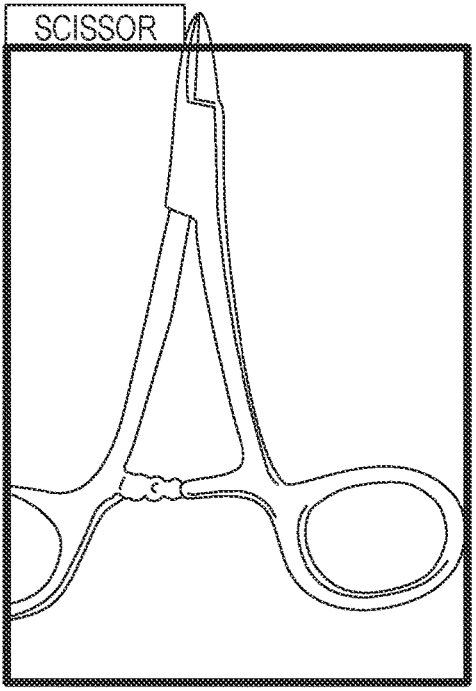
Figure 9:
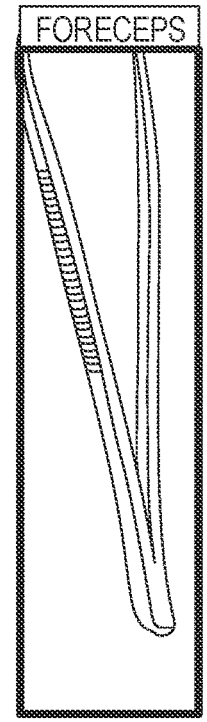
Figure 10:
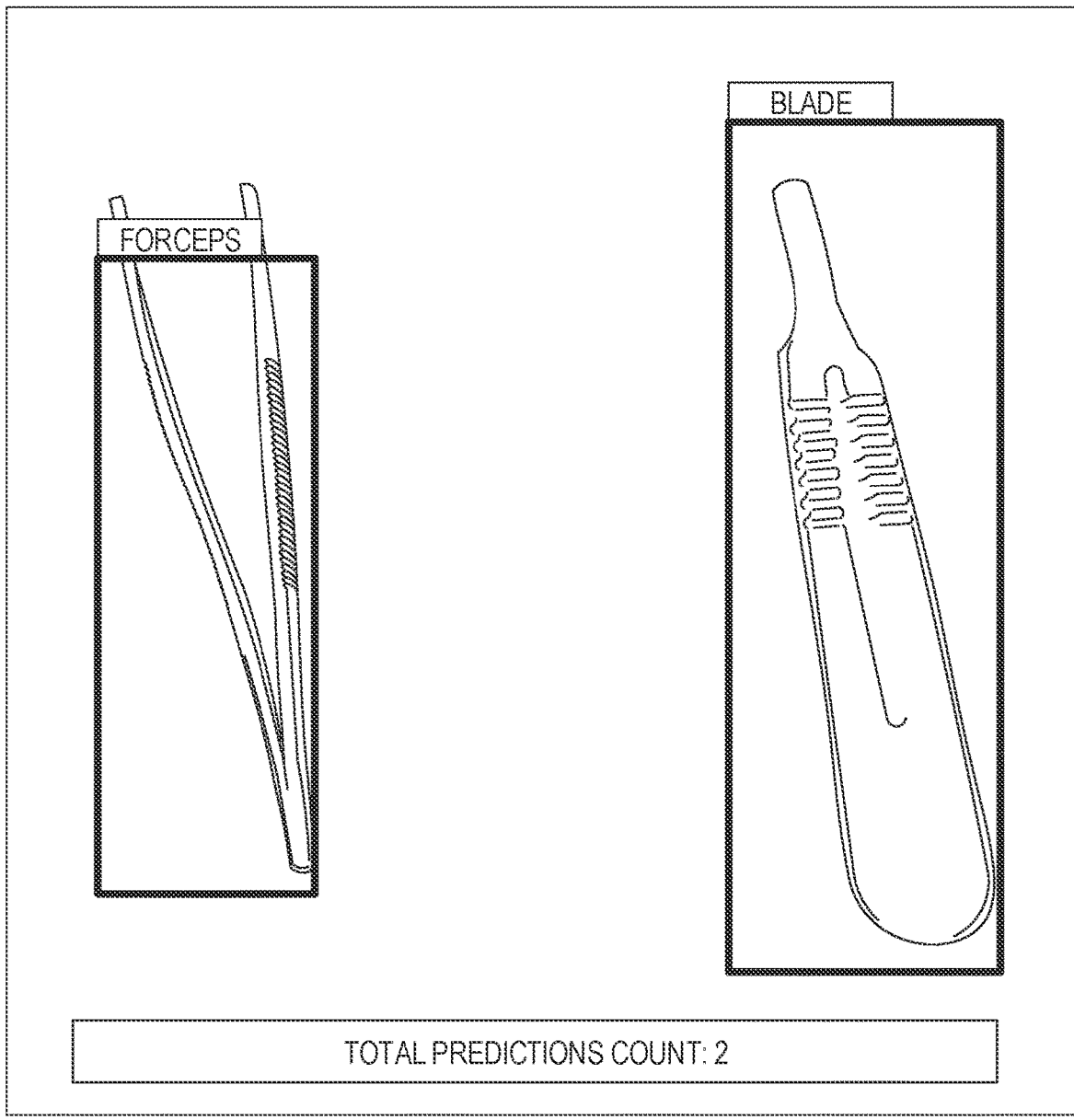

FIGS. 8-10 are screenshots illustrating images that depict instruments and in which the device 130 configured by the app 200, for each image, has added counted quantities of the instruments, individually and by type of instrument, according to some example embodiments.

As illustrated in FIGS. 7-10, the app 200 may configure the device 130 to scan its environment in real time using the camera 240, while continuously running the instrument recognizer 220 (e.g., running the object identifier) such that, when any instruments are captured by the camera 240, the app 200 displays bounding boxes around the instruments, along with their types (e.g., class names) and also along with a count of the total instruments identified in the image (e.g., in the currently displayed frame of video).

In accordance with the techniques discussed herein, the app 200 may configure any suitable device (e.g., the device 130) to use instrument recognition algorithms (e.g., embodied in the instrument recognizer 220, as described above). The app 200 may offer the user 132 an ability to invoke any of multiple modes of operation for the app 200, for the device 130, or for both. As examples, such operating modes may include an operating room fully featured mode (e.g, a full mode, with all features enabled), an operating room partially featured mode (e.g., a light mode, with the most computationally intensive features disabled or uninstalled), a supply chain mode, a post-surgery quality control mode, an orthopedic sales mode, or any suitable combination thereof.

Any one or more of the above-described algorithms for instrument classification or image identification can be independently applied to different use cases in different contexts. Additionally, any one or more of these algorithms can be applied to portions of instruments (e.g., tips of scissors, handles of instruments, or fulcrums of instruments) and accordingly perform portion classification, portion identification, or both, in manners similar to those described herein for instrument classification, instrument identification, or both. Hence, various examples of the instrument recognizer 220 may include an additional artificial intelligent module (e.g., with one or more deep learning networks) trained on instrument portions, and the additional artificial intelligence module can be used to support (e.g., confirm, verify, or modify) classifications, identification, or both, made by a primary artificial intelligence module trained on whole instruments, whole trays, or both.

When these effects are considered in aggregate, one or more of the methodologies described herein may obviate a need for certain efforts or resources that otherwise would be involved in instrument tracking Efforts expended by a user in tracking instruments may be reduced by use of (e.g., reliance upon) a special-purpose machine that implements one or more of the methodologies described herein. Computing resources used by one or more systems or machines (e.g., within the network environment 100) may similarly be reduced (e.g., compared to systems or machines that lack the structures discussed herein or are otherwise unable to perform the functions discussed herein). Examples of such computing resources include processor cycles, network traffic, computational capacity, main memory usage, graphics rendering capacity, graphics memory usage, data storage capacity, power consumption, and cooling capacity.

Figure 11:
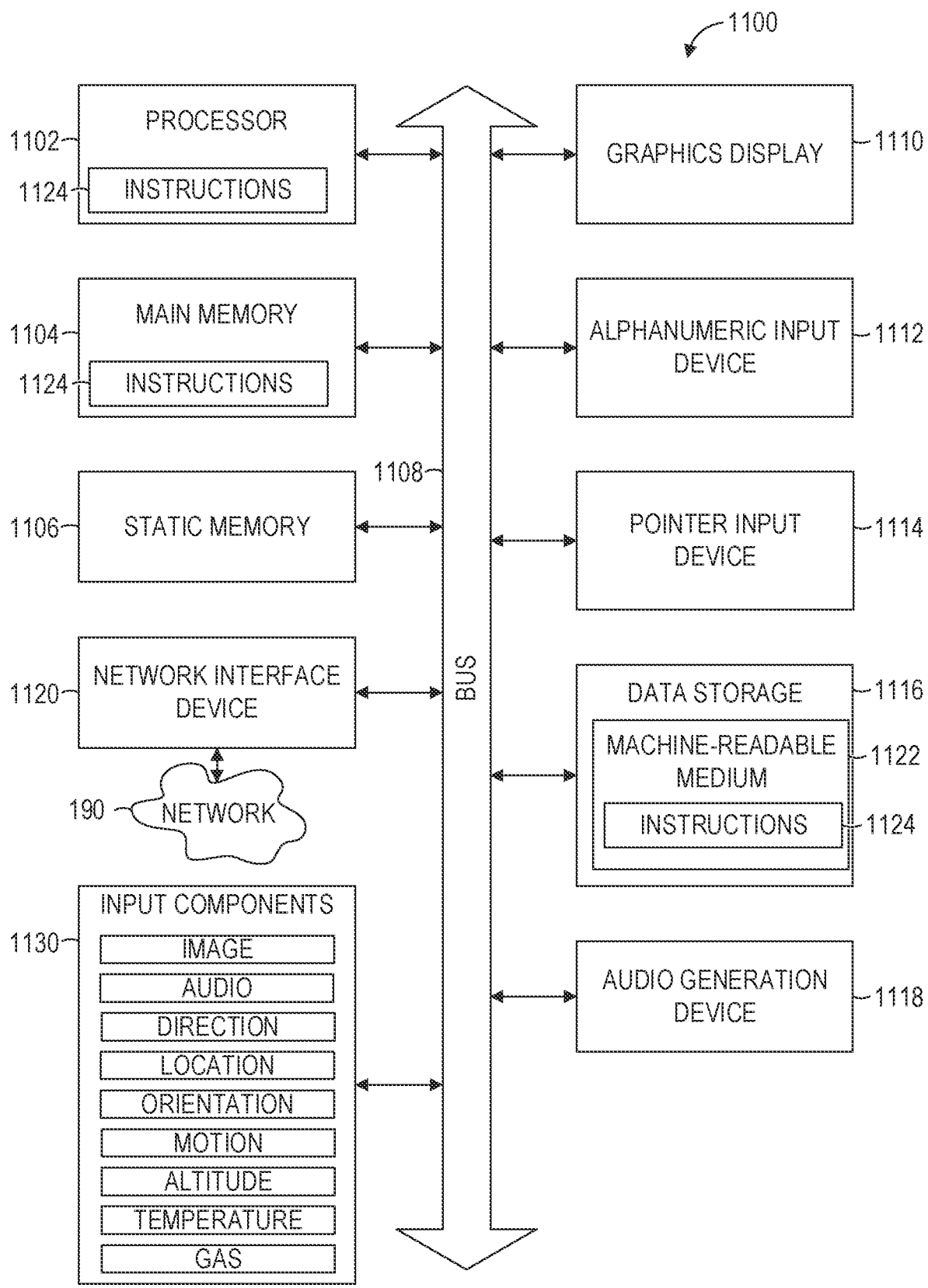
FIG. 11 is a block diagram illustrating components of a machine, according to some example embodiments, able to read instructions from a machine-readable medium and perform any one or more of the methodologies discussed herein.

FIG. 11 is a block diagram illustrating components of a machine 1100, according to some example embodiments, able to read instructions 1124 from a machine-readable medium 1122 (e.g., a non-transitory machine-readable medium, a machine-readable storage medium, a computer-readable storage medium, or any suitable combination thereof) and perform any one or more of the methodologies discussed herein, in whole or in part. Specifically, FIG. 11 shows the machine 1100 in the example form of a computer system (e.g., a computer) within which the instructions 1124 (e.g., software, a program, an application, an applet, an app, or other executable code) for causing the machine 1100 to perform any one or more of the methodologies discussed herein may be executed, in whole or in part.

In alternative embodiments, the machine 1100 operates as a standalone device or may be communicatively coupled (e.g., networked) to other machines. In a networked deployment, the machine 1100 may operate in the capacity of a server machine or a client machine in a server-client network environment, or as a peer machine in a distributed (e.g., peer-to-peer) network environment. The machine 1100 may be a server computer, a client computer, a personal computer (PC), a tablet computer, a laptop computer, a netbook, a cellular telephone, a smart phone, a set-top box (STB), a personal digital assistant (PDA), a web appliance, a network router, a network switch, a network bridge, or any machine capable of executing the instructions 1124, sequentially or otherwise, that specify actions to be taken by that machine.

Further, while only a single machine is illustrated, the term "machine" shall also be taken to include any collection of machines that individually or jointly execute the instructions 1124 to perform all or part of any one or more of the methodologies discussed herein.

The machine 1100 includes a processor 1102 (e.g., one or more central processing units (CPUs), one or more graphics processing units (GPUs), one or more digital signal processors (DSPs), one or more application specific integrated circuits (ASICs), one or more radio-frequency integrated circuits (RFICs), or any suitable combination thereof), a main memory 1104, and a static memory 1106, which are configured to communicate with each other via a bus 1108. The processor 1102 contains solid-state digital microcircuits (e.g., electronic, optical, or both) that are configurable, temporarily or permanently, by some or all of the instructions 1124 such that the processor 1102 is configurable to perform any one or more of the methodologies described herein, in whole or in part. For example, a set of one or more microcircuits of the processor 1102 may be configurable to execute one or more modules (e.g., software modules) described herein. In some example embodiments, the processor 1102 is a multicore CPU (e.g., a dual-core CPU, a quad-core CPU, an 8-core CPU, or a 128-core CPU) within which each of multiple cores behaves as a separate processor that is able to perform any one or more of the methodologies discussed herein, in whole or in part. Although the beneficial effects described herein may be provided by the machine 1100 with at least the processor 1102, these same beneficial effects may be provided by a different kind of machine that contains no processors (e.g., a purely mechanical system, a purely hydraulic system, or a hybrid mechanical-hydraulic system), if such a processor-less machine is configured to perform one or more of the methodologies described herein.

The machine 1100 may further include a graphics display 1110 (e.g., a plasma display panel (PDP), a light emitting diode (LED) display, a liquid crystal display (LCD), a projector, a cathode ray tube (CRT), or any other display capable of displaying graphics or video). The machine 1100 may also include an alphanumeric input device 1112 (e.g., a keyboard or keypad), a pointer input device 1114 (e.g., a mouse, a touchpad, a touchscreen, a trackball, a joystick, a stylus, a motion sensor, an eye tracking device, a data glove, or other pointing instrument), a data storage 1116, an audio generation device 1118 (e.g., a sound card, an amplifier, a speaker, a headphone jack, or any suitable combination thereof), and a network interface device 1120.

The data storage 1116 (e.g., a data storage device) includes the machine-readable medium 1122 (e.g., a tangible and non-transitory machine-readable storage medium) on which are stored the instructions 1124 embodying any one or more of the methodologies or functions described herein. The instructions 1124 may also reside, completely or at least partially, within the main memory 1104, within the static memory 1106, within the processor 1102 (e.g., within the processor's cache memory), or any suitable combination thereof, before or during execution thereof by the machine 1100. Accordingly, the main memory 1104, the static memory 1106, and the processor 1102 may be considered machine-readable media (e.g., tangible and non-transitory machine-readable media). The instructions 1124 may be transmitted or received over the network 190 via the network interface device 1120. For example, the network interface device 1120 may communicate the instructions 1124 using any one or more transfer protocols (e.g., hypertext transfer protocol (HTTP)).

In some example embodiments, the machine 1100 may be a portable computing device (e.g., a smart phone, a tablet computer, or a wearable device) and may have one or more additional input components 1130 (e.g., sensors or gauges). Examples of such input components 1130 include an image input component (e.g., one or more cameras), an audio input component (e.g., one or more microphones), a direction input component (e.g., a compass), a location input component (e.g., a global positioning system (GPS) receiver), an orientation component (e.g., a gyroscope), a motion detection component (e.g., one or more accelerometers), an altitude detection component (e.g., an altimeter), a temperature input component (e.g., a thermometer), and a gas detection component (e.g., a gas sensor). Input data gathered by any one or more of these input components 1130 may be accessible and available for use by any of the modules described herein (e.g., with suitable privacy notifications and protections, such as opt-in consent or opt-out consent, implemented in accordance with user preference, applicable regulations, or any suitable combination thereof).

As used herein, the term "memory" refers to a machine-readable medium able to store data temporarily or permanently and may be taken to include, but not be limited to, random-access memory (RAM), read-only memory (ROM), buffer memory, flash memory, and cache memory. While the machine-readable medium 1122 is shown in an example embodiment to be a single medium, the term "machine-readable medium" should be taken to include a single medium or multiple media (e.g., a centralized or distributed database, or associated caches and servers) able to store instructions. The term "machine-readable medium" shall also be taken to include any medium, or combination of multiple media, that is capable of carrying (e.g., storing or communicating) the instructions 1124 for execution by the machine 1100, such that the instructions 1124, when executed by one or more processors of the machine 1100 (e.g., processor 1102), cause the machine 1100 to perform any one or more of the methodologies described herein, in whole or in part. Accordingly, a "machine-readable medium" refers to a single storage apparatus or device, as well as cloud-based storage systems or storage networks that include multiple storage apparatus or devices. The term "machine-readable medium" shall accordingly be taken to include, but not be limited to, one or more tangible and non-transitory data repositories (e.g., data volumes) in the example form of a solid-state memory chip, an optical disc, a magnetic disc, or any suitable combination thereof.

A "non-transitory" machine-readable medium, as used herein, specifically excludes propagating signals per se. According to various example embodiments, the instructions 1124 for execution by the machine 1100 can be communicated via a carrier medium (e.g., a machine-readable carrier medium). Examples of such a carrier medium include a non-transient carrier medium (e.g., a non-transitory machine-readable storage medium, such as a solid-state memory that is physically movable from one place to another place) and a transient carrier medium (e.g., a carrier wave or other propagating signal that communicates the instructions 1124).

Certain example embodiments are described herein as including modules. Modules may constitute software modules (e.g., code stored or otherwise embodied in a machine-readable medium or in a transmission medium), hardware modules, or any suitable combination thereof. A "hardware module" is a tangible (e.g., non-transitory) physical component (e.g., a set of one or more processors) capable of performing certain operations and may be configured or arranged in a certain physical manner. In various example embodiments, one or more computer systems or one or more hardware modules thereof may be configured by software (e.g., an application or portion thereof) as a hardware module that operates to perform operations described herein for that module.

In some example embodiments, a hardware module may be implemented mechanically, electronically, hydraulically, or any suitable combination thereof. For example, a hardware module may include dedicated circuitry or logic that is permanently configured to perform certain operations. A hardware module may be or include a special-purpose processor, such as a field programmable gate array (FPGA) or an ASIC. A hardware module may also include programmable logic or circuitry that is temporarily configured by software to perform certain operations. As an example, a hardware module may include software encompassed within a CPU or other programmable processor. It will be appreciated that the decision to implement a hardware module mechanically, hydraulically, in dedicated and permanently configured circuitry, or in temporarily configured circuitry (e.g., configured by software) may be driven by cost and time considerations.

Accordingly, the phrase "hardware module" should be understood to encompass a tangible entity that may be physically constructed, permanently configured (e.g., hardwired), or temporarily configured (e.g., programmed) to operate in a certain manner or to perform certain operations described herein. Furthermore, as used herein, the phrase "hardware-implemented module" refers to a hardware module. Considering example embodiments in which hardware modules are temporarily configured (e.g., programmed), each of the hardware modules need not be configured or instantiated at any one instance in time. For example, where a hardware module includes a CPU configured by software to become a special-purpose processor, the CPU may be configured as respectively different special-purpose processors (e.g., each included in a different hardware module) at different times. Software (e.g., a software module) may accordingly configure one or more processors, for example, to become or otherwise constitute a particular hardware module at one instance of time and to become or otherwise constitute a different hardware module at a different instance of time.

Hardware modules can provide information to, and receive information from, other hardware modules. Accordingly, the described hardware modules may be regarded as being communicatively coupled. Where multiple hardware modules exist contemporaneously, communications may be achieved through signal transmission (e.g., over circuits and buses) between or among two or more of the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory (e.g., a memory device) to which it is communicatively coupled. A further hardware module may then, at a later time, access the memory to retrieve and process the stored output. Hardware modules may also initiate communications with input or output devices, and can operate on a resource (e.g., a collection of information from a computing resource).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions described herein. As used herein, "processor-implemented module" refers to a hardware module in which the hardware includes one or more processors. Accordingly, the operations described herein may be at least partially processor-implemented, hardware-implemented, or both, since a processor is an example of hardware, and at least some operations within any one or more of the methods discussed herein may be performed by one or more processor-implemented modules, hardware-implemented modules, or any suitable combination thereof.

Moreover, such one or more processors may perform operations in a "cloud computing" environment or as a service (e.g., within a "software as a service" (SaaS) implementation). For example, at least some operations within any one or more of the methods discussed herein may be performed by a group of computers (e.g., as examples of machines that include processors), with these operations being accessible via a network (e.g., the Internet) and via one or more appropriate interfaces (e.g., an application program interface (API)). The performance of certain operations may be distributed among the one or more processors, whether residing only within a single machine or deployed across a number of machines. In some example embodiments, the one or more processors or hardware modules (e.g., processor-implemented modules) may be located in a single geographic location (e.g, within a home environment, an office environment, or a server farm). In other example embodiments, the one or more processors or hardware modules may be distributed across a number of geographic locations.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and their functionality presented as separate components and functions in example configurations may be implemented as a combined structure or component with combined functions. Similarly, structures and functionality presented as a single component may be implemented as separate components and functions. These and other variations, modifications, additions, and improvements fall within the scope of the subject matter herein.

Some portions of the subject matter discussed herein may be presented in terms of algorithms or symbolic representations of operations on data stored as bits or binary digital signals within a memory (e.g., a computer memory or other machine memory). Such algorithms or symbolic representations are examples of techniques used by those of ordinary skill in the data processing arts to convey the substance of their work to others skilled in the art. As used herein, an "algorithm" is a self-consistent sequence of operations or similar processing leading to a desired result. In this context, algorithms and operations involve physical manipulation of physical quantities. Typically, but not necessarily, such quantities may take the form of electrical, magnetic, or optical signals capable of being stored, accessed, transferred, combined, compared, or otherwise manipulated by a machine. It is convenient at times, principally for reasons of common usage, to refer to such signals using words such as "data," "content," "bits," "values," "elements," "symbols," "characters," "terms," "numbers," "numerals," or the like. These words, however, are merely convenient labels and are to be associated with appropriate physical quantities.

Unless specifically stated otherwise, discussions herein using words such as "accessing," "processing," "detecting," "computing," "calculating," "determining," "generating," "presenting," "displaying," or the like refer to actions or processes performable by a machine (e.g., a computer) that manipulates or transforms data represented as physical (e.g., electronic, magnetic, or optical) quantities within one or more memories (e.g., volatile memory, non-volatile memory, or any suitable combination thereof), registers, or other machine components that receive, store, transmit, or display information. Furthermore, unless specifically stated otherwise, the terms "a" or "an" are herein used, as is common in patent documents, to include one or more than one instance. Finally, as used herein, the conjunction "or" refers to a non-exclusive "or," unless specifically stated otherwise.

The following enumerated descriptions describe various examples of methods, machine-readable media, and systems (e.g., machines, devices, or other apparatus) discussed herein.

A first example provides a method comprising:
accessing, by one or more processors of a machine, a first image capturing a reference set of instruments on a conveyance prior to initiation of a procedure;
identifying, from the first image and by the one or more processors of the machine, first instrument data corresponding to the reference set of instruments;
accessing, by the one or more processors of the machine, a second image capturing instruments on the conveyance after initiation of the procedure;
identifying, from the second image and by the one or more processors of the machine, second instrument data corresponding to the instruments on the conveyance after initiation of the procedure;
comparing, by the one or more processors of the machine, the first instrument data with the second instrument data; and
based on the comparing and by the one or more processors of the machine, causing presentation of a notification that indicates an instrument on the conveyance prior to the initiation of the procedure is absent on the conveyance after the initiation of the procedure.

A second example provides a method according to the first example, further comprising:
accessing reference images of instruments;
identifying instruments in the first image based on the reference images, the first instrument data indicating the identified instruments in the first image; and
identifying instruments in the second image based on the reference images, the second instrument data indicating the identified instruments in the second image.

A third example provides a method according to the first example or the second example, further comprising:
optically recognizing shapes of instruments in the first image to obtain the first instrument data; and
optically recognizing shapes of instruments in the second image to obtain the second instrument data.

A fourth example provides a method according to any of the first through third examples, wherein the first and second images correspond to at least one of a type of the procedure or a performer of the procedure.

A fifth example provides a method according to any of the first through fourth examples, wherein the first instrument data includes a first instrument count, and the second instrument data includes a second instrument count.

A sixth example provides a method according to the fifth example, wherein the comparing of the first instrument data with the second instrument data includes comparing the first instrument count with the second instrument count; and wherein the notification indicates at least one of a total count of missing instruments or a total count of missing instruments having a shared type.

A seventh example provides a method according to any of the first through sixth examples, wherein the procedure includes a surgical procedure performed on a patient by a doctor; the first image captures the reference set of instruments on the conveyance prior to commencement of the surgical procedure on the patient by the doctor; and the second image captures the instruments on the conveyance after completion of the surgical procedure on the patient by the doctor.

An eighth example provides a system (e.g., a computer system) comprising:
one or more processors; and
a memory storing instructions that, when executed by at least one processor among the one or more processors, cause the system to perform operations comprising:
accessing a first image capturing a reference set of instruments on a conveyance prior to initiation of a procedure;
identifying, from the first image, first instrument data corresponding to the reference set of instruments;
accessing a second image capturing instruments on the conveyance after initiation of the procedure;
identifying, from the second image, second instrument data corresponding to the instruments on the conveyance after initiation of the procedure;
comparing the first instrument data with the second instrument data; and
based on the comparing, causing presentation of a notification that indicates an instrument on the conveyance prior to the initiation of the procedure is absent on the conveyance after the initiation of the procedure.

A ninth example provides a system according to the eighth example, wherein the operations further comprise:
optically recognizing shapes of instruments in the first image to obtain the first instrument data; and
optically recognizing shapes of instruments in the second image to obtain the second instrument data.

A tenth example provides a machine-readable medium (e.g., a non-transitory machine-readable storage medium) comprising instructions that, when executed by one or more processors of a machine, cause the machine to perform operations comprising:
accessing a first image capturing a reference set of instruments on a conveyance prior to initiation of a procedure;
identifying, from the first image, first instrument data corresponding to the reference set of instruments;
accessing a second image capturing instruments on the conveyance after initiation of the procedure;
identifying, from the second image, second instrument data corresponding to the instruments on the conveyance after initiation of the procedure;
comparing the first instrument data with the second instrument data; and
based on the comparing, causing presentation of a notification that indicates an instrument on the conveyance prior to the initiation of the procedure is absent on the conveyance after the initiation of the procedure.

An eleventh example provides a method comprising:
accessing, by one or more processors of a machine, a first image captured prior to initiation of a procedure and that depicts a set of instruments available for use in the procedure;
accessing, by the one or more processors of the machine, a second image captured after initiation of the procedure and that depicts a proper subset of the set of instruments depicted in the first image;
determining, by the one or more processors of the machine, that an instrument among the set of instruments depicted in the first image is not depicted among the proper subset of the set of instruments in the second image; and causing, by the one or more processors of the machine, presentation of a notification that indicates the instrument not depicted in the second image is missing from the set of instruments.

A twelfth example provides a method according to the eleventh example, wherein:
the accessing of the first image that depicts the set of instruments includes accessing a reference image that depicts a reference set of instruments.

A thirteenth example provides a method according to the twelfth example, wherein:
the reference image corresponds to at least one of the procedure or a performer of the procedure; and
the accessing of the reference image is based on at least one of the procedure or the performer of the procedure.

A fourteenth example provides a method according to the twelfth example or thirteenth example, wherein:
the reference set of instruments corresponds to at least one of the procedure or a performer of the procedure; and
the accessing of the reference image that depicts the reference set of instruments is based on at least one of the procedure or the performer of the procedure.

A fifteenth example provides a method according to any of the eleventh through fourteenth examples, wherein:
the determining that the instrument among the set of instruments depicted in the first image is not depicted in the second image includes:
optically recognizing a shape of the instrument in the first image; and
failing to optically recognize the shape of the instrument in the second image.

A sixteenth example provides a method according to any of the eleventh through fifteenth examples, wherein:
the determining that the instrument among the set of instruments depicted in the first image is not depicted in the second image includes:
accessing a reference model of the instrument; and
failing to optically recognize each of a plurality of silhouettes of the reference model of the instrument in the second image.

A seventeenth example provides a method according to any of the eleventh through sixteenth examples, wherein:
the determining that the instrument among the set of instruments depicted in the first image is not depicted in the second image includes:
accessing a reference model that represents a reference shape of the instrument depicted in the first image;
accessing depth data that represents current shapes of the proper subset of the set of instruments depicted in the second image; and
comparing the reference shape of the instrument to each of current shapes of the proper subset of the set of instruments.

An eighteenth example provides a method according to any of the eleventh through seventeenth examples, wherein:
the accessing of the first image is performed by capturing a first sequence of first frames prior to the procedure and selecting at least the first image from the captured first sequence; and
the accessing of the second image is performed by capturing a second sequence of second frames after the procedure and selecting at least the second image from the captured second sequence.

A nineteenth example provides a method comprising:
accessing, by one or more processors of a machine, a first image captured prior to initiation of a procedure and that depicts a set of instruments available for use in the procedure;
accessing, by the one or more processors of the machine, a second image captured after initiation of the procedure and that depicts a subset of the set of instruments depicted in the first image;
determining, by the one or more processors of the machine, whether an instrument among the set of instruments depicted in the first image was used or unused in the procedure based on the first and second images; and causing, by the one or more processors of the machine, presentation of a notification that indicates whether the instrument was used or unused in the procedure.

A twentieth example provides a method according to the nineteenth example, wherein:
the subset of the set of instruments is a proper subset of the set of instruments.

A twenty-first example provides a method according to the nineteenth example or the twentieth example, wherein:
the determining of whether the instrument was used or unused in the procedure includes determining whether the instrument moved from a first position within a conveyance depicted in the first image to a second position within the conveyance depicted in the second image.

A twenty-second example provides a method according to any of the nineteenth through twenty-first examples, wherein:
the determining of whether the instrument was used or unused in the procedure includes:
optically recognizing an absence of blood on the instrument depicted in the first image; and
optically recognizing a presence of blood on the instrument depicted in the second image.

A twenty-third example provides a machine-readable medium (e.g., a non-transitory machine-readable storage medium) comprising instructions that, when executed by one or more processors of a machine, cause the machine to perform operations comprising:
accessing a first image captured prior to initiation of a procedure and that depicts a set of instruments available for use in the procedure;
accessing a second image captured after initiation of the procedure and that depicts a proper subset of the set of instruments depicted in the first image;
determining that an instrument among the set of instruments depicted in the first image is not depicted among the proper subset of the set of instruments in the second image; and causing presentation of a notification that indicates the instrument not depicted in the second image is missing from the set of instruments.

A twenty-fourth example provides a machine-readable medium according to the twenty-third example, wherein:
the determining that the instrument among the set of instruments depicted in the first image is not depicted in the second image includes:
optically recognizing a shape of the instrument in the first image; and
failing to optically recognize the shape of the instrument in the second image.

A twenty-fifth example provides a machine-readable medium (e.g., a non-transitory machine-readable storage medium) comprising instructions that, when executed by one or more processors of a machine, cause the machine to perform operations comprising:
accessing a first image captured prior to initiation of a procedure and that depicts a set of instruments available for use in the procedure;
accessing a second image captured after initiation of the procedure and that depicts a subset of the set of instruments depicted in the first image;
determining whether an instrument among the set of instruments depicted in the first image was used or unused in the procedure based on the first and second images; and
causing presentation of a notification that indicates whether the instrument was used or unused in the procedure.

A twenty-sixth example provides a machine-readable medium according to the twenty-fifth example, wherein:
the determining of whether the instrument was used or unused in the procedure includes determining whether the instrument moved from a first position within an conveyance depicted in the first image to a second position within the conveyance depicted in the second image.

A twenty-seventh example provides a system comprising:
one or more processors; and
a memory storing instructions that, when executed by at least one processor among the one or more processors, cause the system to perform operations comprising:
accessing a first image captured prior to initiation of a procedure and that depicts a set of instruments available for use in the procedure;
accessing a second image captured after initiation of the procedure and that depicts a proper subset of the set of instruments depicted in the first image;
determining that an instrument among the set of instruments depicted in the first image is not depicted among the proper subset of the set of instruments in the second image; and causing presentation of a notification that indicates the instrument not depicted in the second image is missing from the set of instruments.

A twenty-eighth example provides a system according to the twenty-seventh example, wherein:
the determining that the instrument among the set of instruments depicted in the first image is not depicted in the second image includes:
accessing a reference model that represents a reference shape of the instrument depicted in the first image;
accessing depth data that represents current shapes of the proper subset of the set of instruments depicted in the second image; and
comparing the reference shape of the instrument to each of current shapes of the proper subset of the set of instruments.

A twenty-ninth example provides a system comprising:
one or more processors; and
a memory storing instructions that, when executed by at least one processor among the one or more processors, cause the system to perform operations comprising:
accessing a first image captured prior to initiation of a procedure and that depicts a set of instruments available for use in the procedure;
accessing a second image captured after initiation of the procedure and that depicts a subset of the set of instruments depicted in the first image;
determining whether an instrument among the set of instruments depicted in the first image was used or unused in the procedure based on the first and second images;
and
causing presentation of a notification that indicates whether the instrument was used or unused in the procedure.

A thirtieth example provides a system according to the twenty-ninth example, wherein:
the determining of whether the instrument was used or unused in the procedure includes:
optically recognizing an absence of blood on the instrument depicted in the first image; and
optically recognizing a presence of blood on the instrument depicted in the second image.

A thirty-first example provides a carrier medium carrying machine-readable instructions for controlling a machine to carry out the operations (e.g., method operations) performed in any one of the previously described examples.

The invention claimed is:

1. A method comprising:
accessing, by one or more processors of a machine, a first image capturing a reference set of instruments on a conveyance prior to initiation of a procedure;
identifying, from the first image and by the one or more processors of the machine, first instrument data corresponding to the reference set of instruments;
accessing, by the one or more processors of the machine, a second image capturing instruments on the conveyance after initiation of the procedure;
identifying, from the second image and by the one or more processors of the machine, second instrument data corresponding to the instruments on the conveyance after initiation of the procedure;
comparing, by the one or more processors of the machine, the first instrument data with the second instrument data to determine whether an instrument among the set of instruments depicted in the first image was used or unused; and
based on the comparing and by the one or more processors of the machine, causing presentation of a notification that indicates whether the instrument among the set of instruments was used or unused during the procedure.

2. The method of claim 1, further comprising:
accessing reference images of instruments;
identifying instruments in the first image based on the reference images, the first instrument data indicating the identified instruments in the first image; and
identifying instruments in the second image based on the reference images, the second instrument data indicating the identified instruments in the second image.

3. The method of claim 1, further comprising:
optically recognizing shapes of instruments in the first image to obtain the first instrument data; and optically recognizing shapes of instruments in the second image to obtain the second instrument data.

4. The method of claim 1, wherein the first instrument data includes a first instrument count, and the second instrument data includes a second instrument count.

5. The method of claim 1, wherein the procedure includes a surgical procedure performed on a patient by a doctor; the first image captures the reference set of instruments on the conveyance prior to commencement of the surgical procedure on the patient by the doctor;

and the second image captures the instruments on the conveyance after completion of the surgical procedure on the patient by the doctor.

6. The method of claim 1, wherein determining whether the instrument was used or unused in the procedure comprises determining whether the instrument moved from a first position within a conveyance depicted in the first image to a second position within the conveyance depicted in the second image.

7. The method of claim 1, wherein determining whether the instrument was used or unused in the procedure comprises:
optically recognizing an absence of blood on the instrument depicted in the first image; and
optically recognizing a presence of blood on the instrument depicted in the second image.

8. A system comprising:
one or more processors; and
a memory storing instructions that, when executed by at least one processor among the one or more processors, cause the system to perform operations comprising:
accessing a first image capturing a reference set of instruments on a conveyance prior to initiation of a procedure;
identifying, from the first image, first instrument data corresponding to the reference set of instruments;
accessing a second image capturing instruments on the conveyance after initiation of the procedure;
identifying, from the second image, second instrument data corresponding to the instruments on the conveyance after initiation of the procedure;
comparing the first instrument data with the second instrument data to determine whether an instrument among the set of instruments depicted in the first image was used or unused; and
based on the comparing, causing presentation of a notification that indicates whether the instrument among the set of instruments was used or unused during the procedure.

9. The system of claim 8, wherein the operations further comprise:
accessing reference images of instruments;
identifying instruments in the first image based on the reference images, the first instrument data indicating the identified instruments in the first image; and
identifying instruments in the second image based on the reference images, the second instrument data indicating the identified instruments in the second image.

10. The system of claim 8, wherein the operations further comprise:
optically recognizing shapes of instruments in the first image to obtain the first instrument data; and
optically recognizing shapes of instruments in the second image to obtain the second instrument data.

11. The system of claim 8, wherein the first instrument data includes a first instrument count, and the second instrument data includes a second instrument count.

12. The system of claim 8, wherein the procedure includes a surgical procedure performed on a patient by a doctor; the first image captures the reference set of instruments on the conveyance prior to commencement of the surgical procedure on the patient by the doctor; and the second image captures the instruments on the conveyance after completion of the surgical procedure on the patient by the doctor.

13. The system of claim 8, wherein the instructions are configured to cause the system to determine whether the instrument was used or unused in the procedure by determining whether the instrument moved from a first position within a conveyance depicted in the first image to a second position within the conveyance depicted in the second image.

14. The system of claim 8, wherein the instructions are configured to cause the system to determine whether the instrument was used or unused in the procedure by optically recognizing an absence of blood on the instrument depicted in the first image, and optically recognizing a presence of blood on the instrument depicted in the second image.

15. A non-transitory machine-readable storage medium comprising instructions that, when executed by one or more processors of a machine, cause the machine to perform operations comprising:
accessing a first image capturing a reference set of instruments on a conveyance prior to initiation of a procedure;
identifying, from the first image, first instrument data corresponding to the reference set of instruments;
accessing a second image capturing instruments on the conveyance after initiation of the procedure;
identifying, from the second image, second instrument data corresponding is the instruments on the conveyance after initiation of the procedure;
comparing the first instrument data with the second instrument data to determine whether an instrument among the set of instruments depicted in the first image was used or unused; and
based on the comparing, causing presentation of a notification that indicates whether the instrument among the set of instruments was used or unused during the procedure.

16. The non-transitory machine-readable storage medium of claim 15, wherein the operations further comprise:
accessing reference images of instruments;
identifying instruments in the first image based on the reference images, the first instrument data indicating the identified instruments in the first image; and
identifying instruments in the second image based on the reference images, the second instrument data indicating the identified instruments in the second image.

17. The non-transitory machine-readable storage medium of claim 15, wherein the operations further comprise:
optically recognizing shapes of instruments in the first image to obtain the first instrument data; and
optically recognizing shapes of instruments in the second image to obtain the second instrument data.

18. The non-transitory machine-readable storage medium of claim 15 wherein the first instrument data includes a first instrument count, and the second instrument data includes a second instrument count.

19. The non-transitory machine-readable storage medium of claim 15, wherein the instructions are configured to cause the machine to determine whether the instrument was used or unused in the procedure by determining whether the instrument moved from a first position within a conveyance depicted in the first image to a second position within the conveyance depicted in the second image.

20. The non-transitory machine-readable storage medium of claim 15, wherein the instructions are configured to cause the machine to determine whether the instrument was used or unused in the procedure by optically recognizing an absence of blood on the instrument depicted in the first image, and optically recognizing a presence of blood on the instrument depicted in the second image.

\* \* \* \* \*